United States Patent
Iris et al.

(10) Patent No.: US 6,403,309 B1
(45) Date of Patent: Jun. 11, 2002

(54) METHODS FOR DETECTION OF NUCLEIC ACID POLYMORPHISMS USING PEPTIDE-LABELED OLIGONUCLEOTIDES AND ANTIBODY ARRAYS

(75) Inventors: Francois J.-M. Iris, Chaville; Jean-Louis Pourny, Neuilly, both of (FR)

(73) Assignee: ValiGen (US), Inc., Newtown, PA (US)

( * ) Notice: Subject to any disclaimer, the term of this patent is extended or adjusted under 35 U.S.C. 154(b) by 0 days.

(21) Appl. No.: 09/272,970

(22) Filed: Mar. 19, 1999

(51) Int. Cl.[7] .................... C12Q 1/68; C12M 1/34; C07H 21/04; C07H 21/02
(52) U.S. Cl. .................. 435/6; 435/7.1; 435/18; 435/287.2; 435/288.3; 536/23.1; 536/24.33
(58) Field of Search ............... 435/6, 5, 7.1, 91.1, 435/91.2, 18, 800, 287.2, 288.3; 536/23.1, 24.33, 24.3, 24.32

(56) References Cited

U.S. PATENT DOCUMENTS

| | | | |
|---|---|---|---|
| 4,843,155 A | | 6/1989 | Chomczynski |
| 4,946,778 A | | 8/1990 | Ladner et al. |
| 5,225,539 A | | 7/1993 | Winter |
| 5,252,743 A | | 10/1993 | Barrett et al. |
| 5,445,934 A | | 8/1995 | Fodor et al. |
| 5,489,678 A | | 2/1996 | Fodor et al. |
| 5,585,089 A | | 12/1996 | Queen et al. |
| 5,610,287 A | | 3/1997 | Nikiforov et al. |
| 5,679,524 A | | 10/1997 | Nikiforov et al. |
| 5,744,305 A | | 4/1998 | Fodor et al. |
| 5,762,876 A | | 6/1998 | Lincoln et al. |
| 5,837,859 A | | 11/1998 | Teoule et al. |
| 5,871,928 A | | 2/1999 | Fodor et al. |
| 6,110,676 A | * | 8/2000 | Coull et al. ............ 435/6 |
| 6,110,684 A | * | 8/2000 | Kemper ................. 435/6 |

FOREIGN PATENT DOCUMENTS

| | | |
|---|---|---|
| EP | 0 370 694 | 5/1990 |
| EP | 0 691 978 | 3/1994 |
| EP | 0 596 028 | 5/1994 |
| WO | WO 93/20233 | * 10/1993 |
| WO | WO 94/22889 | 10/1994 |
| WO | WO 95/12607 | 5/1995 |
| WO | WO 96/40902 | 12/1996 |
| WO | WO 98/26095 | 6/1998 |
| WO | WO 98/59066 | 12/1998 |
| WO | WO 99/04042 | 1/1999 |
| WO | WO 99/36575 | 7/1999 |

OTHER PUBLICATIONS

Lee et al. Allelic discrimination by nick–translation PCR with fluorogenic probes. Nucleic acids Research, vol. 21, No. 16, pp. 3761–3766, Dec. 1993.*

(List continued on next page.)

*Primary Examiner*—Stephanie W. Zitomer
(74) *Attorney, Agent, or Firm*—Pennie & Edmonds LLP

(57) ABSTRACT

The present invention is directed to methods and compositions for use in screening nucleic acid populations for nucleic acid polymorphisms. The methods, referred to generally as ValiGene[SM] Mutation Screening, Peptide-Linked (VGMS-PL) methods, are specifically designed for high-throughput genotype mapping and gene expression analysis of animal and plant nucleic acids without requiring a PCR amplification step. In particular, the methods of the invention utilize oligonucleotide probes labeled with distinguishable and identifiable peptide tags, that are captured on addressable antibody arrays.

37 Claims, 3 Drawing Sheets

BASIC WORKING PRINCIPLE OF VGMS-PL

OTHER PUBLICATIONS

Figure 1:
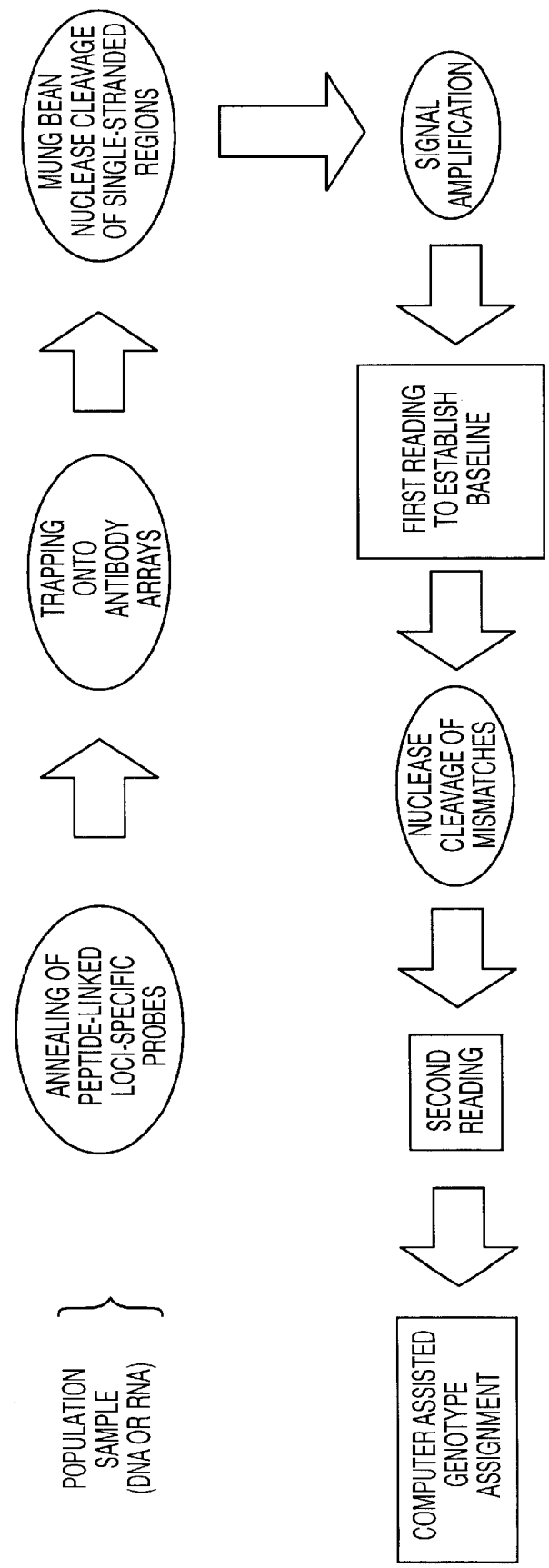

Weiler et al. hybridization based DNA screening on peptide nucleic acid (PNA) oligomer array. Nucleic aicd research. vol. 25, No. 14, pp. 2792–2799, Dec. 1993.*

Alarie et al., 1990, "Evaluation of anitobdy immobilization techniques for fiber optic–based fluoroimmunosensing", Anal. Chim. Acta 229, 169–176.

Bell D., 1997, "Genetic analysis of complex diseases", Science 275:1327.

Bhatia et al., 1989, "Use of thiol–terminal silanes and heterobifunctional cross linkers for immobilization of antibodies on silica surfaces", Analy. Biochem. 178, 408–413.

Bird, 1988, "Single–chain antigen–binding proteins", Science 242:423–426.

Blawas A. & Reichert W., 1998, "Protein patterning", Biomaterials 19:595–609.

Breslow, 1996, "Battling heart disease", Science 272:685–688.

Britten and Davi , 1985 Hybridization Strategy In B.D. Hanes and Higgins, eds., Nucleic Acid Hybridization: A Practical Approach. pp. 3–46 IRL Press, Oxford University Press, Oxford.

Brown et al., 1984, "How LDL receptors influence cholesterol and atherosclerosis", Sci. Amer. 251:58–66.

Brumbaugh et al., 1988, "Continuous, on–line DNA sequencing using oligodeoxynucleotide primers with multiple fluorophores", Proc. Natl. Acad. Sci. (USA), 85:5610–5614.

Chen et al., 1998, "A homogeneous, ligase–mediated DNA diagnostic test", Genome Res. 8:549–556.

Chen et al., 1997, "Fluorescence energy transfer detection as a homogeneous DNA diagnostic method", Proc. Natl. Acad. Sci. 94:10756–10761.

Chomczynski & Sacchi, 1987, "Single–step method of RNA isolation by acid guanidinium thiocyanate–phenol–chloroform extraction", Anal. Biochem. 162:156–159.

Cocuzz, 1989, "A phosphoramidite reagent for automated solid phase synthesis of 5'biotinylated oligonucleotides", Tetrahed. Lett. 30, 6287–6290.

Cole et al., 1985, *Monoclonal Antibodies and Cancer Therapy,* Alan R. Liss, Inc., pp. 77–96.

Cooper T & Matox W, 1997, "The regulation of splice–site selection & its role in human disease", Am. J. Hum. Genet. 61:259–266.

Cooper, 1985, "An estimate of unique DNA sequence heterozygosity in the human genome", Hum. Genet. 69:201–205.

Cotton et al., 1998, "The HUGO Mutation Database Initiative", Science 279:10–11.

Dahlen et al., 1994, "Europium–labeled oligonucleotide hybridization probes: preparation and properties", Bioconjug. Chem. 5:268–72.

Day and Humphries, 1994, "Electrophoresis for genotyping: microtiter array diagonal gel electrophoresis on horizontal polyacrylamide gels, hydrolink, or agarose", Annal Biochem. 222:389–395.

De Meirleir et al., 1994, "Aberrant splicing of exon 6 in the pyruvate dehydrogenase–E1 alpha mRNA linked to a silent mutation in a large family with Leigh's encephalomyelopathy", Pediatr. Res. 36:707–712.

Delamarche et al., 1996, "Immobilization of antibodies on a photoactive self–assembled monolayer on gold", Langmuir 12:1997–2006.

Demple B. & Linn S., "On the recognition and cleavage mechanism of *E. coli* endodeoxyribonuclease V, an possible DNA repair enzyme", J. Biol. Chem.257:2848–2855.

Firestone et al., 1996, "Film architecture in biomolecular assemblies, Effect of linker on the orientation of genetically engineered surface–bound proteins", J. Amer. Chem. Soc. 18, 9033–9041.

Francino P & Ochman H. 1997, "Strand asymmetries in DNA evolution", TIG 13(6):240–245.

Gautier et al., 1987, "Alpha–DNA. IV: Alpha–anomeric and beta–anomeric tetrathymidylates covalently linked to intercalating oxazolopyridocarbazole. Synthesis, physicochemical properties and poly (rA) binding", Nucl. Acids Res. 15:6625–6641.

Gombotz et al., 1991, "Protein adsorption to poly(ethylene oxide) surfaces", J. Biomed. Mater. Res. 25:1547–1562.

Guo G & Weiss B., 1998, "Endonuclease V (nfi) mutant of *escherichia coli* K–12", J. Bacteriology 180(1):46.

Hobbs et al., 1990, "Response by women aged 65–79 to invitation for screening for breast cancer by mammography: a pilot study", Ann. Rev. Genet. 24:133–170.

Huse et al., 1989, "Generation of a large combinatorial library of the immunoglobulin repertoire in phage lambda", Science 246:1275–1281.

Huston et al., 1988, "Protein engineering of antibody binding sites: recovery of specific activity in an anti–digoxin single–chain Fv analogue produced in *Escherichia coli*", Proc. Natl. Acad. Sci. U.S.A. 85:5879–5883.

Ingram, 1957, "Gene mutations in human haemoglobin: the chemical difference between normal and sickle cell haemoglobin", Nature 180:326–328.

Jin et al., 1996, "Glanzmann thrombasthenia. Cooperation between sequence variants in cis during splice site selection", J. Clin. Invest. 98:1745–54.

Krawczak et al., "The mutational spectrum of single base–pair s itutions in mRNA splice of human genes: causes and consequences", Hum. Genet. 90:41–54.

Lamture and Wensel, 1995, "Intensely luminescent immunoreactive conjugates of proteins and dipicolinate–based polymeric Tb (III) chelates", Bioconjug. Chem. 6:88–92.

Li and Selvin, 1997, "Amine–reactive forms of luminescent diethylenetriaminepentacetic aid chelate of terbium ad europium: attachment of DNA and energy transfer measurements", Bioconjug, Chem. 8:127–32.

Lin et al., 1988, "Characterization of immobilized antibodies on silica surfaces", IEEE Trans. Biomed. Eng., 35(6):466–471.

Liu et al., 1997, "Overlapping PCR for bidirectional PCR amplification of specific alleles: a rapid one–tube method for simultaneously differentiating homozygotes and heterozygotes", Genome Res. 7:389–398.

Livak et al., 1995, "Towards fully automated genome–wide polymorphism screening", Nature Genet. 9:341–342.

Lom et al., 1993, "A versatile technique for patterning biomolecules onto glass coverslips", J. Neurosci. Methods 50(3):385–397.

Mooney et al., 1996, "Patterning of functional antibodies and other proteins by photolithography of silane monolayers", Proc. Natl. Acad. Sci. 93:12287–12291.

Morrison et al., 1984, "Chimeric human antibody molecules: mouse antigen–binding domains with human constant region domains", Proc. Natl. Acad. Sci. U.S.A. 81:6851–6855.

Mullis et al., 1986, "Specific enzymatic amplification of DNA in vitro: the polymerase chain reaction", Cold Spring Harbor Symp. Quant. Biol. 51:263–73.

Nelson et al., 1992, "Oligonucleotide labeling methods. 3. Direct labeling of oligonucleotides employing a novel, non–nucleosidic, 2–aminobutyl–1,3–propanediol backbone", Nucl. Acids Res. 20:6253–6259.

Neuberger et al., 1984, "Recombinant antibodies possessing novel effector functions", Nature, 312:604–608.

Olsson et al., 1982, "Human–human monoclonal antibody–producing hybridomas: technical aspects", Meth. Enzymol. 92:3–16.

Owaku et al., 1993, "optical immunosensing for IgG", Sensors & Actuators B, 13–14:723–724.

Pastinen et al., 1996, "Multiplex, fluorescent, solid–phase minisequencing for efficient screening of DNA sequence variation", Clin. Chem. 42:1391–1397.

Persidis A., 1988, "Pharmacogenomics & diagnostics", Nature Biotechnology 16:981.

Pirrung et al., 1996, "A general method for the spatially defined immobilization of biomolecules on glass surfaces using caged'biotin", Bioconjugate Chem. 7:317–321.

Risch and Merikangas, 1996, "The future of genetic studies of complex human diseases", Science 273:1516–1517.

Sarin et al., 1988, "Inhibition of acquired immunodeficiency syndrome virus by oligodeoxynucleoside methylphosphonates", Proc. Nat'l Acad. Sci. U.S.A. 85:7448–7451.

Schena et al., 1995, "Quantitative monitoring of gene expression patterns with a complementary DNA microarray", Science 270:467–470.

Schramm et al., 1992, "Antibody–antigen complex formation with immoblized immunoglobulins", Anal. Biochem. 205, 47–56.

Selkoe, 1997, "Alzheimer's disease: genotypes, phenotypes, and treatments", Science 275:630–631.

Shuber et al., 1997, "High throughput parallel analysis of hundreds of patient samples for more than 100 mutations in multiple disease genes", Hum. Mol. Gen. 6:337–347.

Stein et al., 1988, "Physicochemical properties of phosphorothioate oligodeoxynucleotides", Nucl. Acids Res. 16:3209.

Takeda et al., 1985, "Construction of chimaeric processed immunoglobulin genes containing mouse variable and human constant region sequences", Nature 314:452–454.

Teng et al., 1983, "Construction and testing of mouse—human heteromyelomas for human monoclonal antibody production", Proc. Natl. Acad. Sci. U.S.A. 80:7308–7312.

Tyagi et al., 1998, "Multicolor molecular beacons for allele discrimination", Nature Biotechnol. 16:49–53.

Van Amstel et al., 1996, "Hereditary tyrosinemia type 1: novel misse nonsense and splice consensus mutations in the human fumarylacetoacetate hydrolase gene; variability of the genotype–phenotype relationship", Hum. Genet. 97:51–59.

Wagner et al., 1995, "Mutation detection using immobilized mismatch binding protein (MutS)", Nucl. Acids Res. 23:3944–3948.

Wang et al., 1998, "Association of unconventional myosin MYO15 mutations with human nonsyndromic deafness DFNB3", Science 280:1077–1082.

Ward et al., 1989, "Binding activities of a repertoire of single immunoglobulin variable domains secreted from *Escherichia coli*", Nature 341:544–546.

Weisgraber, 1996, "Human apolipoprotein E: the Alzheimer's disease connection", FASEB J. 10:1485–1494.

Yao and Kow, 1996, "Cleavage of insertion/deletion mismatches, flap and pseudo–Y DNA structures by deoxyinosine 3'–enonuclease from *E. coli*", J. Biol. Chem. 271:30672–6.

Yao M & Kow Y., 1997, "Further characterisation of *E. coli* endonuclease", J. Biol. Chem. 272:30774–79.

* cited by examiner

METHODS FOR DETECTION OF NUCLEIC ACID POLYMORPHISMS USING PEPTIDE-LABELED OLIGONUCLEOTIDES AND ANTIBODY ARRAYS

1. FIELD OF THE INVENTION

The present invention relates to compositions and methods for use in screening nucleic acid populations for nucleotide polymorphisms. The methods, referred to generally as ValiGene[SM] Mutation Screening, Peptide-Linked (VGMS-PL) methods, are specifically designed for high-throughput genotype mapping and gene expression analysis of nucleic acids without requiring a PCR amplification step. In particular, the methods of the invention utilize oligonucleotide probes labeled with distinguishable and identifiable labels, (e.g., peptide tags), that are captured on addressable antibody arrays for analysis (e.g., by fluorescence photometry).

2. BACKGROUND OF THE INVENTION

With the advent of genome-wide sequencing efforts, understanding the molecular basis of all genetic diseases may soon be within reach. Single nucleotide polymorphism (SNP) detection analysis is playing an increasingly powerful role in mapping out the underlying genetic basis of many human diseases.

Approximately 1 in every 1000 nucleotides differs between any two copies of the human genome (Cooper, 1996, Hum. Genet. 69:201–205). Some of these genetic variations, or SNPs, lead to differences in the proteins encoded by such genes. Others are "silent", residing in non-protein coding regions of the genome. Such SNPs are now being used, for example, to diagnose genetic disorders, determine a predisposition to genetic disease, identify or determine the ancestry of a genetic sample, or correlate genetic sequences with phenotypic conditions, such as complex disorders or drug response and toxicity (Risch and Merikangas, 1996, Science 273:1516–1517). This powerful combination of genetic and molecular biological approaches is changing the face of drug development. SNPs have been correlated with Huntington's disease, Alzheimer's disease, and various forms of breast cancer. In the emerging field of pharmacogenomics, specific SNPs are being used to determine and predict a patient's susceptibility to diseases as well as drug toxicity and reponse. Pharmacogenomics can also provide tools to identify new targets for designing drugs and to optimize the use of existing drugs. The hope is that this understanding will ultimately lead to the early diagnosis, prevention, and treatment of genetic diseases.

Single nucleotide polymorphisms can be identified by a number of methods, including DNA sequencing, restriction enzyme analysis, or site-specific hybridization. However, high-throughput genome-wide screening for SNP and mutations requires the ability to simultaneously analyze multiple loci with high accuracy and sensitivity. To increase sensitivity, current high-throughput methods for single nucleotide detection rely on a step that involves amplification of the target nucleic acid sample, usually by the polymerase chain reaction (PCR) (see, e.g., Nikiforov et al., U.S. Pat. No. 5,679,524 issued Oct. 21, 1997; McIntosh et al., PCT publication WO 98/59066 dated Dec. 30, 1998; Goelet et al., PCT publication WO 95/12607 dated May 11, 1995; Wang et al., 1998, Science 280:1077–1082; Tyagi et al., 1998, Nature Biotechnol. 16:49–53; Chen et al., 1998, Genome Res. 8:549–556; Pastinen et al., 1996, Clin. Chem. 42:1391–1397; Chen et al, 1997, Proc. Natl. Acad. Sci. 94:10756–10761; Shuber et al., 1997, Hum. Mol. Gen. 6:337–347; Liu et al., 1997, Genome Res. 7:389–398; Livak et al., Nature Genet. 9:341–342; Day and Humphries, 1994, Annal. Biochem. 222:389–395). However, the fidelity of the PCR technique is limited. Combinations of pairs of PCR primers tend to generate spurious reaction products. Moreover, the number of errors in the final reaction product increases exponentially with the each round of PCR amplification after an error is introduced into a DNA sample. Thus, PCR error can be a substantial drawback when searching for rare variations in nucleic acid populations.

For all of the reasons addressed above, a highly sensitive, highly specific, PCR-free method for high-throughput detection of nucleic acid variations is urgently needed. This invention provides such a method, as described in detail below.

Citation or discussion of a reference herein shall not be construed as an admission that such reference is prior art to the present invention.

3. SUMMARY OF THE INVENTION

The present invention provides methods for detection of single nucleotide polymorphisms (SNPs) and other variations in nucleic acid populations. The methods of the present invention for high-throughput PCR-free screening are used for detection of alterations and polymorphisms as well as for analysis of gene expression, both qualitative and quantitative, directly from cellular total RNA. The methods may be used, for example, to diagnose disorders, determine predisposition to genetic diseases, determine identity or ancestry, or correlate genetic sequences with phenotypic conditions.

In a specific embodiment, the invention relates to methods for efficient, sensitive, high-throughput addressable-array based screens using SNP-specific oligonucleotide probes having distinguishable and identifiable peptide tags to detect polymorphisms in nucleic acid target molecules. First, SNP-specific peptide-linked oligonucleotide probes, comprising distinguishable markers, are hybridized to a target nucleic acid sample. Next, any hybrid molecules formed are captured on high-density addressable antibody arrays and processed by enzymes that recognize and cleave the captured hybrid molecules at mismatched base pairs. Finally, markers present on the cleaved hybrid molecules are then detected and analyzed to identify any polymorphic site(s) within a specific target nucleic acid molecule of interest.

The present methods offer several advantages over the currently available technologies for genotype detection. First, the methods described herein allow detection of genetic variation using minimal amounts of genetic material without requiring a PCR amplification step, avoiding the introduction of new mutations into the sample being tested. In other genotyping methods, a PCR amplification step is typically used to amplify the signal of a given target sequence within a nucleic acid sample to allow detection. In the present invention, it is the signals that are amplified from a number of limited targets. This allows reliable SNP detection using minimal amounts of genetic material from a variety biological sources, such as biopsies of tissue from a patient with a potential genetic disorder. Second, unlike in other methods of genotype mapping, nucleic acid hybridization takes place in solution, eliminating the need to immobilize a hybridization partner. Solution hybridization is more efficient than hybridization with one immobilized partner, resulting in increased efficiency of mismatch detection. Third, the addressable chip array allows a flexible detection system for high-throughput genotype analysis. Multiple SNP sites can be screened simultaneously from a patient or genetic sample, or alternatively, a single SNP site in many different DNA samples, can be tested simultaneously. For example, in one embodiment, detection of multiple polymorphisms in a target nucleic acid sample is possible in a single run. Multiple probes can be individually prepared, each probe having a unique peptide label and a sequence corresponding to a polymorphic site to be detected. Such multiple probes can be hybridized in "batch" with the target nucleic acid sample. In another embodiment, multiple target nucleic acid samples can be screened simultaneously for the presence or absence of a single SNP locus.

Throughout this application reference is made to peptide labels and antibodies for binding said labels. In addition to peptide-antibody combinations, it will be understood by those skilled in the art that any label can be used, in combination with a suitable binding partner. Examples of such labels and binding partners include, but are not limited to, digoxigenin-antidigoxigenin, biotin-streptavidin, ligand (e.g. hormone)-receptor and carbohydrate-lectin combinations.

The term "polymorphism" as used herein refers to the presence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism, or SNP, is a single base-pair variant, typically the substitution of one nucleotide by another nucleotide at the polymorphic site. Deletion of a single nucleotide or insertion of a single nucleotide, also give rise to single nucleotide polymorphisms. In the context of the present invention, "single nucleotide polymorphism" (SNP) refers to a single nucleotide substitution. Typically, between different genomes or between different individuals, the polymorphic site may be occupied by two different nucleotides. It is to be understood that while the terms "SNP" and "SNP detection" are periodically used throughout the application for purposes of clarity and simplicity of description, the invention term encompasses methods for detection of single nucleotide polymorphisms, as well as double and multiple nucleotide polymorphisms. In various embodiments, the SNP detections methods are also used to detect deletions and insertions in nucleic acid sequences.

The SNP detection methods described herein utilize nucleotide polymorphism-specific probes. The nucleotide polymorphism-specific probe comprises one or more distinguishable "markers". A marker is a nucleotide residue that is incorporated into the probe, preferably during synthesis of the oligonucleotide, that either is 1) covalently bound to a detectable label (e.g. a fluorophore), or 2) is covalently bound to an affinity group (e.g. biotin) that is labeled post-synthesis of the nucleic acid by contacting said affinity group with a labeled cognate binding partner. A detectable label may include but is not limited to a luminescent compound, a chromophore, a fluorescent compound, a radioactive isotope or group containing same, or a nonisotopic label, such as an enzyme or dye. Thus, a detectable label may be directly linked to a nucleotide or indirectly linked, e.g., by its presence on a partner molecule that binds to an affinity group directly linked to the nucleotide.

The invention provides a method for high-throughput nucleotide polymorphism analysis of a nucleic acid sample from a subject comprising contacting a plurality of peptide-labeled oligonucleotide probes with the nucleic acid sample in solution, under conditions conducive to hybridization of the probes to nucleic acid in the sample; and detecting one or more probes of the plurality that hybridize to nucleic acid in the sample using an antibody array comprising antibodies immunospecific to one or more of the peptide labels. In one embodiment of this method, the detecting one or more probes is carried out without using PCR or MutS, an *E. coli* mismatch binding protein that recognizes and binds to nucleic acids containing mismatched base pairs.

The invention further provides a method for screening a nucleic acid sample from one or more subjects for the presence of a polymorphism comprising the following steps in the order stated: a) contacting the nucleic acid sample in solution with one or more nucleotide polymorphism-specific peptide-labeled oligonucleotide probes, under conditions conducive to hybridization of the probes to nucleic acid in the sample; each probe comprising a first marker covalently attached to a first detectable label, and a second marker covalently attached to a second detectable label that produces a signal distinguishable from the first detectable label; such that one or more hybrid molecules are formed between the nucleic acid and one or more oligonucleotide probes; b) capturing at least one of the one or more hybrid molecules on a solid phase surface; c) contacting the solid phase surface with mung bean nuclease, under conditions wherein the nuclease is active; d) removing material not bound to the solid phase surface; e) detecting or measuring from the solid phase surface a first signal from the first detectable label and a second signal from the second detectable label; f) cleaving the hybrid molecules on the solid phase surface at mismatched base pairs; and g) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein a difference between the first ratio and the second ratio indicates that a polymorphism is identified.

In another embodiment, the invention provides a method for screening a nucleic acid sample from one or more subjects for the presence of a polymorphism comprising the following steps in the order stated: a) contacting the nucleic acid sample in solution with one or more nucleotide polymorphism-specific peptide-labeled oligonucleotide probes under conditions conducive to hybridization of the probes to nucleic acid in the sample; each probe comprising a first and a second marker; such that one or more hybrid molecules are formed between the nucleic acid and one or more nucleotide polymorphism-specific oligonucleotide probes; b) capturing at least one of the one or more hybrid molecules on a solid phase surface; c) contacting the solid phase surface with mung bean nuclease, under conditions wherein the nuclease is active; d) removing material not bound to the solid phase surface; e) contacting the solid phase surface with (i) a first partner molecule with the ability to specifically bind the first marker, and (ii) a second partner molecule with the ability to specifically bind the second marker, said first partner molecule comprising a first detectable label and said second partner molecule comprising a second detectable label that produces a signal distinguishable from the first detectable label; f) removing material not bound to the solid phase surface; g) detecting or measuring from the solid phase surface a first signal from the first detectable label and a second signal from the second detectable label; h) cleaving the hybrid molecules on the solid phase surface at mismatched base pairs; and i) detecting or measuring from the solid phase surface a third signal from the detectable label and a fourth signal from the second detectable label, determining a first ratio of the second signal to the first signal, and a second ratio of the fourth signal to the third signal, and comparing the first ratio to the second ratio, wherein a difference between the first ratio and the second ratio indicates that a polymorphism is identified. In one embodiment of these methods the first or second marker is covalently attached to a biotin moiety and the first or second partner molecule is avidin or streptavidin. In another embodiment, the first or second marker is covalently attached to a carbohydrate moiety and the first or second partner molecule is a lectin. In another embodiment, the first partner molecule is an antibody that binds specifically to the first marker and the second partner molecule is an antibody that binds specifically to the second marker.

In another embodiment, a method is provided for screening a nucleic acid sample from one or more subjects for the presence of a polymorphism comprising the following steps in the order stated: a) contacting the nucleic acid sample in solution with one or more nucleotide polymorphism-specific peptide-labeled oligonucleotide probes, under conditions conducive to hybridization of the probes to nucleic acid in the sample; each probe comprising a first and a second marker; such that one or more hybrid molecules are formed between the nucleic acid and one or more nucleotide polymorphism-specific oligonucleotide probes; b) capturing at least one of the one or more hybrid molecules on a solid phase surface; c) contacting the solid phase surface with mung bean nuclease, under conditions wherein the nuclease is active; d) removing material not bound to the solid phase surface; e) contacting the solid phase surface with a first primary partner molecule, with the ability to bind the first marker, and a second primary partner molecule with the ability to bind the second marker; f) removing material not bound to the solid phase surface; g) contacting the solid phase surface with (i) a first secondary partner molecule, with the ability to bind the first primary partner molecule, said first secondary partner molecule comprising a first detectable label, and (ii) a second secondary partner molecule, with the ability to bind the second primary partner molecule, said second secondary partner molecule comprising a second detectable label that produces a signal distinguishable from the first detectable label; h) removing material not bound to the solid phase surface; i) detecting or measuring from the solid phase surface a first signal from the first detectable label and a second signal from the second detectable label; j) cleaving the hybrid molecules on the solid phase surface at mismatched base pairs; and k) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein a difference between the first ratio and the second ratio indicates that a polymorphism is identified. In one embodiment, the first or second marker is covalently attached to a biotin moiety and the first or second primary partner molecule is avidin or streptavidin. In another embodiment, the first or second marker is covalently linked to a carbohydrate moiety and the first or second primary partner molecule is a lectin. In yet another embodiment, the first and second primary partner molecules are distinct primary antibodies, and the first and second secondary partner molecules are distinct secondary antibodies.

The invention further provides a composition comprising one or more nucleotide polymorphism-specific peptide-labeled oligonucleotide probes bound to one or more antibodies of an antibody array.

In one embodiment of these methods, at least one of the one or more nucleotide polymorphism-specific peptide-labeled oligonucleotide probes comprises: a) a peptide covalently attached to the 5' end of the oligonucleotide; b) a first marker at the penultimate 5' position of the oligonucleotide; and c) a second marker at the 3'-end of the oligonucleotide.

In another embodiment of these methods, the solid phase surface comprises a plurality of loci, wherein each locus is capable of specifically binding to one of the one or more oligonucleotide probes via the peptide of the peptide-labeled oligonucleotide and wherein the peptide is covalently attached to the 5' end of the oligonucleotide. In one embodiment, the first or second marker is covalently attached to a carbohydrate moiety and the first or second partner molecule is a lectin.

In another embodiment, either or both the first detectable label or the second detectable label is an enzyme, a fluorophore, a chemiluminescent label, or a radioisotope. In another embodiment, either or both the first detectable marker or the second detectable marker is a fluorophore.

In various embodiments of the invention, the signals are measured by comparing the first ratio to the second ratio, wherein the first ratio at least 35% greater than the second ratio indicates that a polymorphism is identified.

In one embodiment, the solid phase surface comprises a plurality of loci, wherein each locus comprises an antibody specific to one or more of the peptides of the peptide-labeled oligonucleotide probes. In another embodiment, the solid phase surface is a plastic chip. In another embodiment, the solid phase surface is the well of a microtiter plate. In another embodiment, the nucleic acid in the sample is less than 2 µg. In another embodiment, the nucleic acid in the sample is selected from the group consisting of genomic DNA and cDNA. In another embodiment, the nucleic acid in the sample is genomic DNA. In another embodiment, the nucleic acid in the sample is cDNA. In another embodiment, the nucleic acid in the sample is double stranded DNA. In another embodiment, the nucleic acid in the sample is single stranded DNA. In another embodiment, cleaving the hybrid molecules at mismatched base pairs is carried out by contacting said hybrid molecules with one or more specific nucleases under conditions that allow cleavage of said hybrid molecules at mismatched base pairs. In another embodiment, cleaving the hybrid molecules at mismatched base pairs is carried out by contacting said hybrid molecules with E. coli endonuclease V and S1 nuclease under conditions that allow cleavage of said hybrid molecules at mismatched base pairs. In another embodiment, the first and second detectable labels are fluorophores that absorb at the same wavelength but emit at a distinct frequency.

In various embodiments, the invention encompasses methods for detecting or measuring the presence of an alternatively spliced RNA transcript in a that an alternatively spliced RNA transcript is in the sample.

In one embodiment, the subject is a plant. In another embodiment, the subject is a virus, a bacterium, a yeast, or a fungus. In another embodiment, the subject is a mammal. In another embodiment, the subject is equine, porcine, ovine, bovine, camnie, feline, or human. In another embodiment, the subject is a human. In another embodiment, the subject is a plurality of human subjects that exhibit a phenotype of interest.

It is to be understood, that while a SNP-specific probe is represented throughout this application as having two markers, SNP probes comprising 3, 4, or more differentially-labeled markers are also within the scope of the invention. For example, such markers may be placed at locations within the sequence of an oligonucleotide to allow detection of alternate mismatched base pairs or splice junction sequences.

The methods of the invention can be used for direct, PCR-free, genotype mapping, as well as quantitative genomic analysis of allele amplification and loss-of heterozygosity phenomena. The invention further provides a method for detecting and measuring RNA in a sample from a subject comprising the method described above, wherein the SNP-specific oligonucleotide probe comprises the sequence of a known RNA transcript or a known splice-site junction sequence. Such methods can be used to monitor gene expression, both qualitatively and quantitatively, in very small amounts of RNA sample. In one embodiment, the sample is total cellular RNA extracted from a tissue sample or biopsy. In another embodiment, such methods are used in situ to monitor gene expression within histological preparations for diagnostic and prognostic purposes.

4. BRIEF DESCRIPTION OF THE DRAWINGS

FIG. 1. Schematic representation of the VGMS-PL method.

Figure 2:
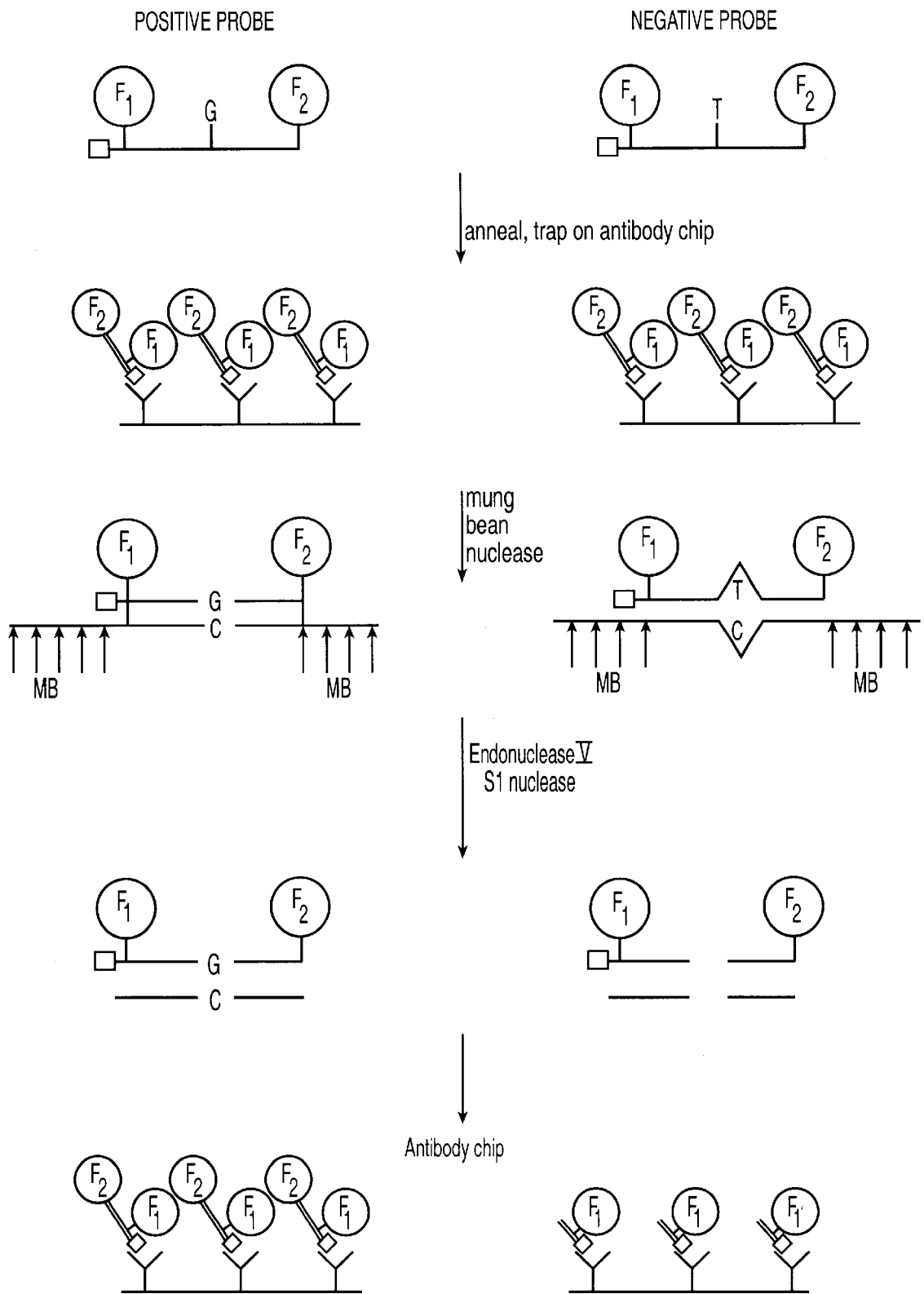

FIG. 2. Method for genotype mapping. This method may use positive and negative oligonucleotide probes, each labeled with a peptide (open box) and two distinct fluorophores ($F_1$ and $F_2$).

Figure 3:
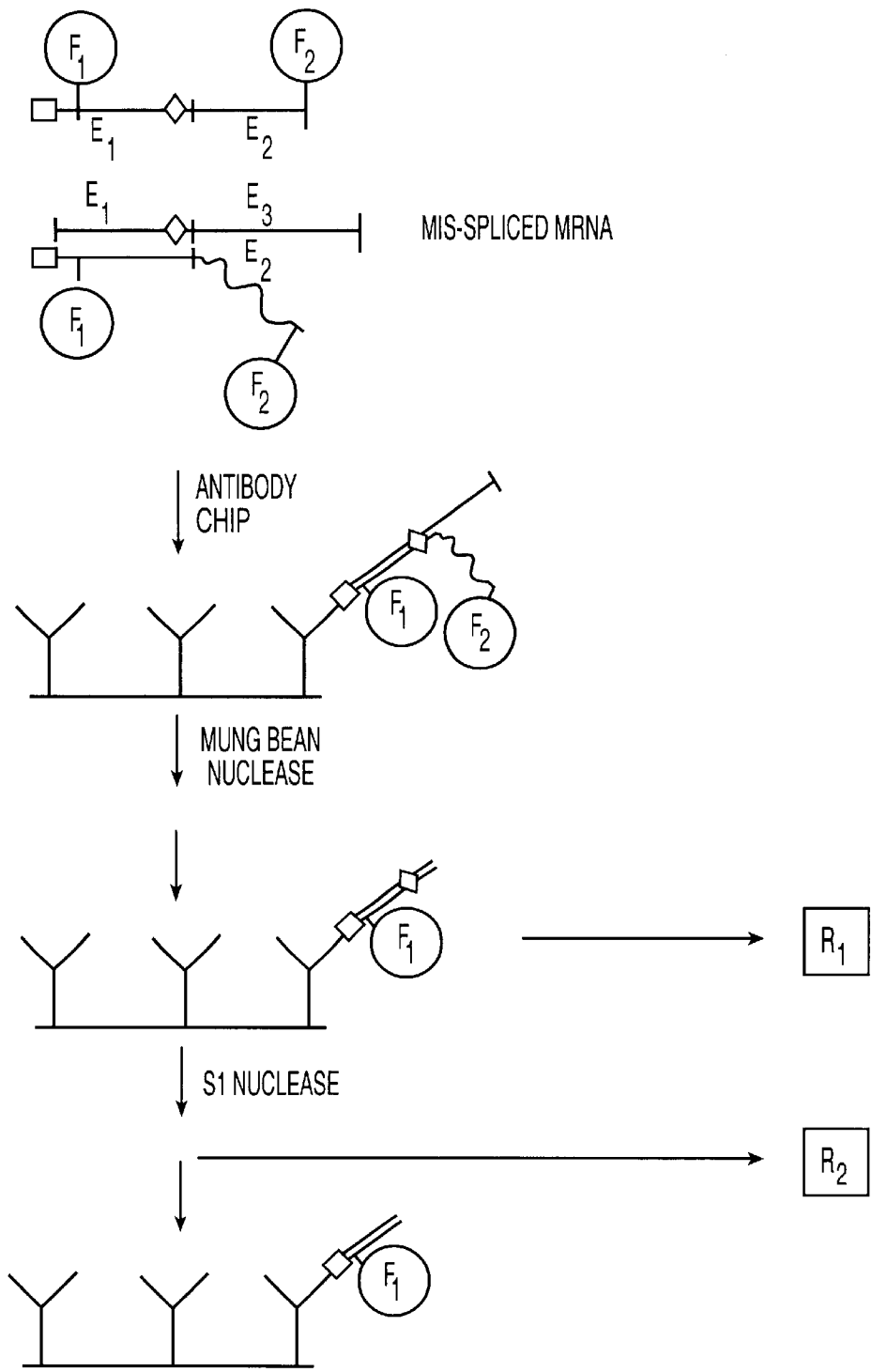

FIG. 3. Schematic representation of the method for gene expression analysis.

5. DETAILED DESCRIPTION OF THE INVENTION

The present invention provides methods referred to generally as ValiGene$^{SM}$ Mutation Screening, Peptide-Linked methods (VGMS-PL methods) for identifying polymorphisms present in populations of nucleic acids. The methods may be used for, for example, determining drug response and toxicity, diagnosing genetic disorders, determining predisposition and risk factors for genetic diseases, determining an individual's identity or ancestry, and correlating genetic sequences with physical disorders or syndromes.

In currently available genotyping methods, a PCR step is typically used to increase the amount of a given target within a genomic sample by amplification of the entire sample to increase its detection. In the present invention, detection is increased by amplification of the signals from a number of limited targets, obviating the need for a PCR amplification step. Signal amplification is achieved by incorporation of affinity groups into the peptide-labeled oligonucleotide probe, and, in later steps, contacting said affinity groups with partner molecules having detectable labels.

The present invention utilizes solution hybridization and cleavage by endonucleases to recognize and detect mismatches. The invention thereby permits avoidance of the use of E. coli mismatch binding proteins such as MutS, an E. coli mismatch binding protein that recognizes and binds to nucleic acids containing mismatched base pairs, which has been used in the past for mismatch detection methods (Wagner et al., 1995, Nucl. Acids Res. 23:3944–3948; Wagner et al. EPO 596 028 B1 and PCT 94/08022).

Specifically, the methods disclosed herein below employ nucleotide polymorphism-specific probes, comprising peptide-linked oligonucleotides having distinguishable markers, as hybridization probes for target nucleic acid molecules. The basic working principle of the PCR-free direct SNP detection method is outlined in FIG. 1. A nucleic acid sample, taken from an individual subject or a population of individual subjects, is annealed to a peptide-linked oligonucleotide probe specific for a genetic locus of interest. For example, such a locus can be a SNP, where the nucleic acid sample is genomic DNA. In an alternative embodiment, where the nucleic acid sample being assayed is RNA, the locus can be a splice site. The annealed probe:target nucleic acid hybrid is then trapped on a solid phase surface, and enzymatically treated to eliminate free probe. A preferred, but optional, signal amplification step is performed, prior to the reading the signals from the probe's 5'- and 3'- end distinguishable markers. The solid phase surface is then treated with a set of enzymes that specifically digests the hybrids at mismatched base pairs, and a second signal is recorded. Analysis of the readouts from the hybrids before and after their digestion at mismatched base pairs allows one to determine the presence of, and in various embodiments, precisely quantitate, the presence of a SNP or splice site in the genetic loci of interest. In one embodiment, the hybrid molecules are captured on high density addressable arrays and analyzed by enzymes that recognize and cleave the captured hybrid molecules at mismatched base pairs. The detectable labels present on the cleaved hybrid molecules are then detected and analyzed to identify polymorphic sites within the specific target nucleic acid molecule of interest.

In the various embodiments of the present invention, labeled oligonucleotides are used as polymorphism-specific hybridization probes. In addition to a peptide label used for capturing a probe on an addressable antibody array, such probes are also labeled with markers to detect hybridization with target nucleic acids at various steps of the process. The basic working principle of the VGMS-PL methods is set forth in FIG. 1. A diagram of PCR-free analysis following exposure to genotype mapping analysis is set forth in FIG. 2. Representative positive and negative probes are illustrated in the top panel of FIG. 2. Details of the method are described in detail herein below.

5.1 OLIGONUCLEOTIDE PROBES

In various embodiments of the present invention, peptide-labeled SNP-specific or locus-specific oligonucleotides are used as hybridization probes to target and detect polymorphic sequences. In a preferred embodiment, an SNP-specific probe comprises a synthetic oligonucleotide with three properties (a positive and negative probe is depicted in the top panel of FIG. 2). First, a peptide label is linked to the 5' end of the oligonucleotide (indicated by the open box in FIG. 2). Second, a first marker ($F_1$), which may be a detectable label or, alternatively, an affinity label that can bind to a partner molecule such as an antibody or affinity partner linked to such a first marker, is located on the penultimate deoxyribose base at the 5' end of the oligonucleotide (indicated by $F_1$ in FIG. 2). Third, a second marker ($F_2$), distinguishable from the first marker, is located on the last deoxyribose base at 3' end of the oligonucleotide (indicated by $F_2$ in FIG. 2).

Polymorphism-specific oligonucleotide probes may be designed to correspond to any nucleic acid sequence, preferably a region known or suspected to contain a polymorphism. Numerous such clinically important SNPs are known. For example, SNPs in apolipoprotein genes, such as apolipoprotein E variants, are implicated in diseases such as atherosclerosis (see Breslow, 1996, Science 272:685–688) and Alzheimer's disease (Selkoe, 1997, Science 275: 630–631; Weisgraber, 1996, FASEB J. 10:1485–1494). Mutation in apolipoproteins and the low density lipoprotein (LDL) receptor gene is common in patients with familial hypercholesterolemia (Hobbs et al., 1990, Ann. Rev. Genet. 24:133–170; Brown et al., 1984, Sci. Amer. 251:58–66). Polymorphisms in the β-globin gene locus are also well known; for example, a single base pair mutation in the β-globin gene is responsible for the substitution of the amino acid valine in place of glutamic acid, resulting in sickle cell anemia (Ingham, 1957, Nature 180:326–328).

Any gene known or suspected to contain a polymorphic site may be used as a target nucleic acid in the methods of the present invention. Amino acid sequences and nucleotide sequences of known or suspected SNP sites are generally available in sequence databases, such as GenBank, or the HUGO database initiative, which is establishing a mutational database as a source of common variants of human disease (Cotton et al, 1998, Science 279:10–11). Computer programs, such as Entrez, can be used to browse the database and retrieve any nucleotide or amino acid sequence data of interest (see http://www.ncbi.nlm.nih.gov/Entrez). These databases can also be searched to identify sequences with various degrees of similarities to a query sequence using programs, such as FASTA and BLAST, which rank the similar sequences by alignment scores and statistics.

The SNP-specific probe comprises one or more distinguishable "markers". A marker is a nucleotide residue that is incorporated into the probe, preferably during synthesis of the oligonucleotide (see Section 5.4.3), that either is 1) covalently bound to a detectable label (e.g. a fluorophore) or, 2) is covalently bound to an affinity group (e.g. biotin) that is labeled post-synthesis of the nucleic acid by contacting said affinity group with a labeled cognate binding partner. A detectable label may include but is not limited to a luminescent compound, a chromophore, a fluorescent compound, a radioactive isotope or group containing same, or a nonisotopic label, such as an enzyme or dye. Thus, a detectable label may be directly linked to a nucleotide or indirectly linked, e.g., by its presence on a partner molecule that binds to an affinity group directly linked to the nucleotide. For example, affinity groups or partner molecules that may be used include, but are not limited to biotin, avidin, streptavidin, digoxygenin, haptens, and monoclonal and polyclonal primary or secondary antibodies.

Where two or more markers are present on a single SNP-specific probe, it is important that the two markers are distinguishable. Assays for such distinguishable markers are well known in the art (see, e.g., Harlow and Lane, 1988, *Antibodies: A Laboratory Manual*, Cold Spring Harbor Laboratory Press, Cold Spring Harbor, N.Y., Chapter 14). In a preferred embodiment, this is accomplished by the use of distinguishable partner molecules that bind to different affinity groups that are linked to the marker residue of the probe. For example, the 3' marker of the SNP-specific probe may be linked to a biotin molecule. Streptavidin, a binding partner molecule of biotin, may be linked to an enzyme label, such as horse radish peroxidase (HRP), and used as an affinity binding partner to specifically bind to the biotin-linked marker. To differentially label the markers, the 5' marker of the SNP-specific probe may be linked to a chelate of divalent or trivalent cations ($Ni^{2+}$, $Cu^{2+}$, $Eu^{3+}$, etc., Dahlen et al., 1994, Bioconjug. Chem. 5:268–72; Li and Selvin, 1997, Bioconjug. Chem. 8:127–132), and a PDLS-coupled globular proteins such as ovalbumin, thyroglobulin etc., and used to specifically bind the chelate marker. PLDS, a polymer of lysine, dipicolinate, and succinate, binds divalent and trivalent cations with high affinity and strongly enhances the visible luminescence they emit when excited with ultraviolet light (Lamture and Wensel, 1995, Bioconjug. Chem. 6:88–92).

In another embodiment, distinguishable markers of a specific probe comprise different fluorophores that emit at different frequencies. Details of the methods used for labeling, signal amplification, and signal detection are described in Section 5.4.

In the most preferred embodiment, SNP-specific probes comprise two distinguishable, detectable affinity labels. In another embodiment, the SNP-specific probe comprises 3, 4, or more differentially labeled markers. Such markers may be placed at locations within the sequence of an oligonucleotide to allow detection of alternate mismatched base pairs or splice junction sequences.

In various embodiments of the invention more than one probe may be used in a single reaction to target more than one polymorphism along the same molecule. Where a mixture of probes is to be used in a single reaction, prior analysis is recommended to minimize interactions between probes and between target fragments, and to ensure similar ΔG characteristics among probes. Such prior analysis of oligonucleotide probes is well known in the art.

5.2 METHODS FOR PCR-FREE GENOTYPE MAPPING

In this embodiment, the methods of the invention are used to detect polymorphic sites, e.g., SNPs, in a DNA sample. The methods may be used to detect single mismatches between a SNP-specific oligonucleotide probe and a target molecule, or to distinguish between single mismatches, double mismatches, or multiple mismatches.

Generally, the method for PCR-free genotype mapping of a DNA sample comprises the following steps: 1) contacting a target DNA with a SNP-specific peptide-labeled oligonucleotide probe comprising a first and a second marker; 2) capturing the annealed hybrids on a solid phase surface; 3) treating the solid phase surface with mung bean nuclease; 4) removing material not bound to the solid phase surface; 5) detecting a signal from the first and second markers; 6) cleaving the probe DNA at any mismatched base pair present; and 7) detecting another signal from the first and second markers.

In the first step, the target DNA is prepared from the sample. The target DNA can be obtained from a biological sample, such as, but not limited to, whole blood, plasma, serum, skin, saliva, urine, lymph fluid, cells obtained from biopsy aspirate, tissue culture cells, media, or non-biological samples such as food, water, or other material. Methods for preparation of DNA from such sources are well known to those of skill in the art (see, e.g., Current Protocols in Molecular Biology series of laboratory technique manuals, 1987–1994 Current Protocols, 1994–1997 John Wiley and Sons, Inc.).

In one embodiment, the target DNA is a fragment of genomic DNA. In another embodiment, the test DNA is cDNA. In another embodiment, the target DNA is a mixed population of genomic DNAs derived from a plurality of subjects of interest, for example, subjects afflicted with a particular disorder.

Target DNA is prepared for hybridization by fragmenting the DNA to an average length of 300 base pairs. In a preferred embodiment, this is accomplished by treating with one or more restriction endonucleases prior to annealing with the probe, to generate fragments of appropriate length. The restriction enzymes are chosen to recognize and cleave a recognition site that does not appear within any SNP-specific probe being used. Such treatment preferably yields DNA fragments in the size range of approximately 100 to 1000 base pairs base pairs, more preferable in the range of 200 to 500 base pairs, most preferably, approximately 300 base pairs. Many restriction enzymes, preferably restriction enzymes with four-base recognition sites, are known in the art and commercially available and can be used for this purpose. In an alternative embodiment, DNA is fragmented by sonication to shear DNA molecules to an average size of 300 base pairs.

The DNA fragments are then mixed with peptide-labeled SNP-specific oligonucleotide probes under conditions that allow hybridization to occur. Exemplary conditions for hybridizations are as follows. Preferably, 300 ng of genomic DNA (about $9\times10^4$ copies of target gene containing SNP of interest) are mixed with 100 fg of probes (about 3.5×106 copies of probe) in a total volume of 5 ul in a buffer containing 10 mM Tris-HCl (pH 7.5); 1 mM EDTA, 50 mM NaCl; and 1 mMCTAB. The mixture is denatured, by heating to 98° C. for 5 minutes, and allowed to renature by incubating the mix at 68 ° C. for 20 minutes. To optimize the results, the stringency can be adjusted. Such methods for adjustment of hybridization stringency are routine and well known in the art (see, e.g., Sambrook et al., 1989, Molecular Cloning, A Laboratory Manual, 2d Ed., Cold Spring Harbor Laboratory Press, Cold Spring Harbor, N.Y.; Ausubel et al., eds., in the Current Protocols in Molecular Biology series of laboratory technique manuals, 1987–1994 Current Protocols, 1994–1997 John Wiley and Sons, Inc). Salt concentration, melting temperature, the absence or presence of denaturants, and the type and length of nucleic acid to be hybridized (e.g., DNA, RNA, PNA) are some of the variables considered when adjusting the stringency of a particular solution hybridization reaction according to methods known in the art (Ausubel et al 1987–1994, p. 2.10.7–2.10.16; Britten and Davidson, 1985, Hybridization Strategy In B. D. Hanes and S. J. Higgins, eds., Nucleic Acid Hybridization: A Practical Approach. p. 3–46 IRL Press, Oxford University Press, Oxford; Mullis et al, 1986, Cold Spring Harbor Symp. Quant. Biol. 51:263–73).

In the second step, the annealed hybrids are captured on a solid phase surface. In one embodiment, where a single probe is used, the solid phase surface can be the wells of a microtiter dish. In an exemplary, non-limiting example, the wells of a microtiter plate (Maxisorb) are coated with 100 µl of an anti-peptide antibody diluted to a concentration of 4 mg/ml in 0.1 M $Na_2CO_3$—$NaHCO_3$ (pH 9.1) for 1.5 hours at 37° C. The plate may then be stored overnight at 4° C. Each well is washed 4 times with 200 µl PBS; 0.1% Tween 20 (Sigma); 10 mM EDTA. The wells are then incubated for 2 hours in 100 µl PBS; 3% BSA [bovine serum albumin (Sigma)] at room temperature to block non-specific binding sites, and washed again as previously described.

The reannealed mixture is brought to a final volume of 120 µl with PBS, transferred to the antibody coated well and incubated at 37° C. for 45 mins. The wells are then washed thoroughly (3 to 4 times) in 200 µl PBS; 0.1% Tween20; 10 mM EDTA to remove unbound nucleic acids, such as all target molecules that have not hybridized to a probe having a peptide-label.

In another embodiment, where multiple probes are captured and analyzed together in batch or "multiplex", the solid phase surface comprises a plurality of loci, each locus having an antibody having specific affinity for a peptide linked to an SNP specific probe (i.e. antibody-specific chip). A detailed description of such an array and methods for its construction are described in Section 5.5. The chip can be prepared as prepared for and bound to annealed probe as described for the microtiter plate above.

In the third step, the solid phase surface is treated with a single-stranded nuclease such as mung bean nuclease, to cleave the single-stranded regions on hybrid molecules and to destroy all non-hybridized probes. Mung bean nuclease is a single-strand specific DNA and RNA endonuclease which removes single-stranded extensions from the ends of DNA and RNA duplex molecules, leaving blunt ends, and leaving internal mismatches shorter than three consecutive bases in double stranded DNA:DNA or DNA:RNA hybrids intact. By way of an example, the wells are filled with 150 µl of buffer containing 0.05 units of mung bean nuclease and incubated at 37° C. for 15 mins and the wells are then washed 4 times with 200 µl phosphate buffered saline (PBS; 150 mM NaCl-10 mM Na-$PO_4$, pH 7.4). After this treatment, all target:probe hybrids will contain both the 5' and 3' markers irrespective of the presence or absence of SNP mismatches. Only in those hybrids which contain mismatches greater than three consecutive bases will the 5' and 3' markers be separated from each other.

The chip is rinsed thoroughly as in step 2, and, in step 5, signals are detected from the markers of an SNP oligonucleotide probe. If the markers were not directly labeled, they can be labeled at this point with any affinity labeling method known in the art. In a preferred embodiment, a partner molecule comprising a detectable label is added to specifically bind an affinity group. For example, the 3' marker of the SNP-specific probe may be linked to a biotin molecule. Streptavidin, a binding partner molecule of biotin, may be linked to an enzyme label, such as horse radish peroxidase (HRP), and used as an affinity binding partner to specifically bind to the biotin-linked marker. In a specific embodiment, 120 µl of a $1\times10^{-5}$ dilution of Amdex reagent, a streptavidin-linked, agarose-bound, aggregate of about 100 molecules of horse radish peroxidase. After 30 min incubation at 25° C., the wells are washed 4 times with 200 µl PBS to remove excess streptavidin HRP, and 160 µl of TMB (tetramethyldecanoic acid, a substrate for horse radish peroxidase) solution is added. The resulting colorimetric reaction is allowed to proceed for 5 mins., 60 µl of liquid is transferred to an uncoated well (of a fresh microtiter plate) to which 25 µl of 1M sulfuiric acid is added to fix colorimetric development. The intensity of this first reaction is read at 450 nm in a plate reader spectrophotometer. The second marker, the 5' label, may be linked to a chelate of divalent or trivalent cations ($Ni^{2+}$, $Cu^{2+}$, $Eu^{3+}$, etc., Dahlen et al, 1994, Bioconjug. Chem. 5:268–72; Li and Selvin, 1997, Bioconjug Chem. 8:127–32). A PDLS-coupled globular proteins such as ovalbumin, thyroglobulin etc, may be used to specifically bind the chelate marker (Lamture and Wensel, 1995, Bioconjug Chem., 6:88–92). PLDS, a polymer of lysine, dipicolinate, and succinate, binds divalent and trivalent cations with high affinity and strongly enhances the visible luminescence they emit when excited with ultraviolet light (Lamture and Wensel, 1995, Bioconjug. Chem. 6:88–92).

In another embodiment, a primary antibody comprising a detectable label is added to specifically bind one or both of the first and second markers. In yet another embodiment, a primary antibody may be added, washed, and followed by addition of a secondary antibody labeled with a detectable label. Such labeling and detection methods are well known in the art, and are further described in Sections 5.4.1 and 5.4.2.

The first "baseline" reading is taken to measure the probe's 3' and 5' markers. The signal is normalized by comparing the reading obtained to the reading obtained from a "control' sample. In such control sample, an oligonucleotide having the sequence of the non-polymorphic site is hybridized to a sample having the non-polymorphic sequence. This reading serves as a measure of the amount of starting material present before the mismatch detection analysis. Here, the probes that produce both signals are hybridized to homologous DNA targets, and probes that produce only 5' signal are hybridized to targets that contain a deletion or an insertion, spanning at least three consecutive bases, relative to the probe sequence. This reading also serves as a baseline reading to normalize samples for differences between various SNP-specific probes in antibody binding affinities.

In the sixth step, the hybrids are digested with one or more enzymes to cleave at mismatched base-pairs. In the preferred embodiment, the deoxyinosine 3' endonuclease *E. coli* endonuclease V (endoV) and S1 nuclease (S1) are used. EndoV, the product of the *E. coli* nfi gene (also known as dI Endo, GenBank accession number U00006), is a deoxyinosine 3' endonuclease that recognizes and nicks DNA containing deoxyinosine residues, single base mismatches, insertion/deletion mismatches, apurinic sites, flaps, and pseudo-Y structures (Demple and Linn, 1982, J. Biol. Chem. 257:2848–55; Yao and Kow, 1996, J. Biol. Chem. 271:30672–6; Yao and Kow, 1997, J. Biol. Chem. 272:30774–79). In this embodiment, Endo V will cleave a mismatched hybrid at the phosphodiester bond of the target strand (non-probe) 3' to the mismatch, either immediately adjacent to or one nucleotide removed, depending on the sequence context of the mismatched base pair. S1 nuclease cleaves across from the single-stranded nick introduced by Endo V, producing a double stranded break. Thus, when a SNP is present, cleavage by Endo V and S1 nuclease dissociates the 3' marker from the 5' marker. When a SNP is not present, the 3' and 5' markers remain associated with the same molecule.

In one embodiment, the wells of the microtiter dish are filled with 120 µl of a reaction buffer containing 0.001 units of S1 nuclease and 0.05 units of endonuclease V. The reaction is allowed to proceed for 15 mins at 37° C. and the wells are then washed as described previously. In an alternative embodiment, where the method is being performed in multiplex, the antibody chip containing the trapped hybrids is placed in a 37° C. reaction bath containing 0.01 units/ml of S1 nuclease and 0.5 units/ml of endo V, and allowed to incubate 12–15 minutes. The washes are accomplished by immersing in a bath of PBS.

In step 7, the signal is developed again, and a second reading is taken. In one embodiment, for example 160 µl of TMB solution is added and the resulting calorimetric reaction is allowed to proceed for 5 mins. 40 µl of 1M sulphuric acid is added and the intensity of the colorimetric development in this second reaction is read as before. In the alternative embodiment, the antibody array is re-developed and the signal recorded. Array coordinates where the intensity of the 3' signal remains unchanged contain hybridized genomic sequence identical to the probes; coordinates where the 3' signal has disappeared but the 5' signal intensity is unchanged contain hybridized genomic sequence non-identical to the probes, and coordinates where the 3' signal intensity has fallen by more than 35% contain hybridized genomic fragments that are heterozygous with respect to the probes. In another embodiment, coordinates where the 3' signal intensity has fallen by more than 25% contain hybridized genomic fragments that are heterozygous with respect to the probes. In another embodiment, coordinates where the 3' signal intensity has fallen by more than 20% contain hybridized genomic fragments that are heterozygous with respect to the probes.

The example in Section 6 demonstrates how one analyzes the signals to detect the presence of a polymorphic site.

In various embodiments, the method is used for multiplex SNP screening. As used herein "multiplex" means simultaneous screening for the presence of more than one SNP site in a single nucleic acid target or a single SNP site in more than one target nucleic acid. In one embodiment, for example, the SNP detection method is used to screen a nucleic acid sample from a single subject for variations across a spectrum of SNP sites. This embodiment of the method may be useful for various purposes, including diagnosing illness, determining a subject's predisposition to genetic disorders, determining a patient's tolerance or toxicity to a drug treatment, and for identifying or determining the ancestry of a subject. In this embodiment, a library of SNP-specific peptide-labeled oligonucleotides is used to probe a single DNA sample for the presence of SNPs. A library of SNP-specific peptide-labeled oligonucleotides, comprising pairs of "positive" probes and "negative" probes of known SNP sequences is used to screen the nucleic acid of a single patient. Hybridizations may be performed in batch, annealing many probes to target nucleic acid in a single mixture. The product is analyzed on addressable antibody arrays, each probe identifiable by its array "address".

In another embodiment, the SNP detection method can be used for multiplex screening to phenotype/genotype association analysis. In this embodiment, a target DNA sample comprises a plurality of DNA molecules derived from a population of individuals afflicted with a disorder of interest, for example, arthritis, asthma, or cancer. A control DNA sample comprises DNA molecules derived from a non-afflicted populations. The two populations can be screened in multiplex with a number of SNP probes, and the results compared between the two populations.

In yet another embodiment, the SNP detection method can be used for multiplex screening of a number of individuals for one or more SNP sites. This method may be useful for example, for diagnostic screening large numbers of patients for a genetic disorder, for drug sensitivity, for blood type, etc. In this embodiment, a SNP-specific probe corresponding to a specific SNP may be linked with any number of different peptide labels. Each SNP probe is annealed to a different sample of target nucleic acid separately, so that each sample is differentially labeled. The samples may then be processed together "in batch" and detected and analyzed using addressable antibody arrays.

The addressable array chip can be regenerated and used repeatedly. For example, peptides can be released by containing a pH gradient over the chip causing the antibodies to release the trapped peptides. The chip is then thoroughly rinsed in PBS for storage or immediate reuse.

5.3 METHOD FOR ANALYSIS OF GENE EXPRESSION USING ADDRESSABLE ANTIBODY ARRAYS

In another embodiment of the invention, methods are provided to monitor gene expression events both qualitatively and quantitatively using peptide-labeled oligonucleotide probes and addressable array analysis. The method described herein can be used, for example, to detect or measure the level of an alternatively spliced or mis-spliced RNA in a tissue sample, or to directly monitor qualitative and quantitative gene expression levels in tissue biopsies or in histological preparations. Such biopsies and histological preparations may be taken from a patient with a suspected genetic disorder, for example, to identify the presence of mutations therein. Peptide-labeled oligonucleotides further labeled with fluorescent labels may be used to monitor such known sites of potential genetic variation, particularly at RNA splice junctions.

Particularly interesting targets are known mutations occurring at intron-exon boundaries that lead to aberrantly spliced mRNAs and result in a broad spectrum of genetic disorders. Mutations commonly occur at such splice-site junction sequences, the region of MRNA spanning the boundary of two exons, formed by a splicing event that removes an intervening sequence of non-coding RNA from a precursor MRNA molecule. Indeed, fifteen percent of all point mutations that result in human genetic disease create an RNA splicing defect (Krawczak et al., 1992, Hum. Genet. 90:41–54). Such splicing mutations frequently affect exon sequences near the intron/exon borders; many of these splice-site mutations are "silent" mutations, resulting in no alteration in the primary amino acid sequence of the encoded protein. Some non-limiting examples include: a G→A mutation in the integrin GPIIIa gene resulting in thrombocytopenia (Jin et al., 1996, J. Clin. Invest. 98:1745–54); a C→T mutation in the gene for fumarylacetoacetate hydrolase resulting in hereditary tyrosinemia (van Amstel et al., 1996, Hum. Genet. 97:51–59); an A→G mutation in pyruvate dehydrogenase E1a resulting in encephalomyelpathy (de Meirleir et al., 1994, Pediatr. Res. 36:707–712); and numerous others (see generally, Cooper and Mattox, 1997, Am. J. Hum. Genet. 61:259–266).

A splice-site probe is designed to span a splice-site junction sequence of a given RNA where either a genomic splice site mutation or an alternative splicing event is known or suspected to occur. A diagrammatic representation of such a mutation, and the splice-site oligonucleotide probe that spans the splice junction between exon1 and exon 2 is shown in FIG. 3.

Total ribonucleic acid (RNA) may be isolated from a tissue sample by a variety of methods known in the art, depending on the source and amount of cells available. Purified RNA can be prepared from tissue samples recovered from a biopsy, from tissue culture cells, etc. Procedures described in standard treatises (e.g., Methods in Enzymology, 1987, volume 154, Academic Press; Sambrook et al, 1989, supra; and Ausubel et al, supra) may be followed to carry out routine molecular biology reactions in purification of total nuclear and cytoplasmic RNA. Methods described in detail infra are for illustration only and not by way of limitation. Various RNA preparation systems that are commercially available may also be used according to the manufacturer's instructions for isolating and purifying the RNA to be used in the methods of the invention. It is preferable to obtain high quality RNA that is of high molecular weight in order to recover RNA containing even rarely expressed gene products. To prepare quality RNA, methods that provide complete lysis of cells and rapid inactivation of nucleases are preferred. Many such methods are known in the art. For example, one single-step RNA preparation method uses the strong chaotropic agent, guanidinium isothiocyanate, together with a mild detergent and $\Delta$-mercaptoethanol or dithiothreitol to denature proteins and inactivate nucleases, and purification of the RNA by ultracentrifugation (Chomczynski & Sacchi, 1987, Anal. Biochem. 162:156–159; Chomczynski, 1989, U.S. Pat. No. 4,843,155). This method may also be used especially when isolating RNA from small quantities of cellular material.

The purified RNA is next heated to 65° C. in hybridization buffer (for e.g., 10–50 $\mu$g RNA in 150 mM KCl, 10 mM TrisCl pH 8.3, 1 mM EDTA) to destroy all secondary structures, and an aliquot of the entire collection of probes is added to the mixture. The RNA is then mixed with the probes, and slow-cooled to room temperature to allow hybridization to occur. In the preferred embodiment, to identify and measure RNA transcripts, the SNP detection method described in Section 5.2 is exactly followed, substituting SNP-specific probes with splice-site probes and using RNA target nucleic acids instead of DNA target nucleic acids. After the hybridization reaction, the sample is exposed to a solid phase surface comprising a binding partner to the peptide label of the oligonucleotide. In various embodiments, for example, the solid phase surface may be a microtiter plate or, for purposes of multiplex gene expression analysis, an addressable antibody array (e.g., on a plastic chip).

The chip is then treated with mung bean nuclease, which cleaves single stranded regions but does not recognize or cleave mismatched base pairs. A first reading is taken ($R_1$ in FIG. 3). This initial reading is taken at the emission wavelengths specific to the two markers present on the probe, preferably labeled with fluorophores, to identify any addressable loci which retain probes that emit at both wavelengths. The initial reading provides an internal baseline, representing the number of RNA molecules captured by the probes. Where a splice event that would result in the formation of the splice-site junction corresponding to a given probe has not occurred in a given sample, such treatment results in partial digestion of the probe and the release of the 3' probe fragment, comprising the $F_2$ fluorophore. The probe remaining after the mung bean nuclease treatment will have lost the $F_2$ fluorophore if the RNA in the sample was incorrectly spliced or alternatively spliced at the splice junction corresponding to the sequence of the oligonucleotide probe (see example in FIG. 3). An alternatively spliced transcript is thereby identified. A sample expressing such RNAs is a candidate for possessing a splice site mutation at the genomic DNA level. The sample is then treated with $E.$ $coli$ endonuclease V (Endo V) plus S1 nuclease (S1) and a second reading is taken ($R_2$ in FIG. 3). Analysis of the readout is carried out as described in Section 5.2.

In an alternative embodiment, excess fluorescently-labeled "empty" probe in the hybridization mixture may be eliminated after the annealing step, to reduce their contribution to the signal in the final product. This may be accomplished, for example, by passing the mixture of RNA and probes over a hydroxyapatite column. Single-stranded probes are trapped in the column, while annealed probes bound to RNA appear in the column flow-through. In another embodiment, empty probe may be separated from hybridized probe by electrophoresis. Such electrophoresis may be accomplished, for example, by a lateral electrophoresis step carried out within a chamber connecting the hybridization vessel and the chip. In another embodiment, an "anti-probe" is used to eliminate the fluorescent signal from excess probe. The anti-probe comprises an oligonucleotide complementary to the peptide-labeled probe that has two fluorescent quenchers matched to the fluorophores present on the probe of interest. The anti-probe is added and annealed to the reaction in order to "mop up" the fluorescence from excess probe.

5.4 METHODS FOR LABELING AND DETECTION OF THE OLIGONUCLEOTIDE PROBE

Labeling, and signal amplification, and detection methods are important for increasing the sensitivity of the PCR-free high-throughput methods of the invention. Signal amplification and increased detection methods allow greater detection of nucleic acid sequences present in low abundance or in small amounts of tissue sample, as well as facilitate multiplex screening of larger sample sizes in a single run. Methods for labeling probes with detectable labels, amplifying and detecting the signal, preparing oligonucleotides, and linking oligonucleotides to peptides are described herein below.

5.4.1 LABELING METHODS

A "label" or a "detectable label" refers to a moiety, such as a luminescent, fluorescent, or radioactive isotope or group containing same, and nonisotopic labels, such as enzymes or dyes. For the embodiments presented herein, where two or more markers are present on a single probe, it is important that the two detectable labels are distinguishable. This may be accomplished, for example, by using different fluorophores that emit at different frequencies, or by using affinity partner molecules containing different fluorophores, as discussed in Section 5.4.2, or by using different types of luminescent agents, enzymes, or dyes.

The oligonucleotide probe may be labeled with a detectable label either directly or indirectly. In a preferred embodiment, the SNP-specific oligonucleotide probe is labeled indirectly by incorporating an affinity group into the oligonucleotide probe during its synthesis (for methods for synthesizing oligonucleotides, see Section 5.4.3, below). A partner molecule specifically recognizes and binds to the affinity group. The partner molecule can comprise a detectable label, such as a fluorophore, coupled to the affinity binding partner. Alternatively, a second partner molecule having affinity for the first partner molecule (such as a secondary antibody) can be used. In this case the second, and not the first, affinity binding partner will comprise the detectable label. Indirect affinity labeling methods are well known in the art (see, generally, Current Protocols in Immunology, Coligan et al., eds.,1997, John Wiley & Sons, Inc. U.S.A., pp. 8.10.12–8.10.21).

In a preferred embodiment, a peptide-labeled oligonucleotide is labeled with biotinylated nucleotides and detected using a streptavidin-linked detectable compound. Biotinylated oligonucleotides are well known in the art. For example, an oligonucleotide may be biotinylated using a biotin-NHS ester procedure. Alternatively, biotin may be attached during oligonucleotide synthesis using a biotin phosphoramidite (Cocuzza, 1989, Tetrahed. Lett. 30, 6287–6290). One such biotin phosphoramidite available from Glen Research is 1-dimethoxytrityloxy-2-(N-biotinyl-4-aminobutyl)-propyl-3-O-(2-cyanoethyl)-(N,N-diisopropyl)-phosphoramidite. This compound also has a branch point to allow further additions. The branched spacer used in this biotin phosphoramidite has been described by Nelson et al. (1992, Nucl. Acids Res. 20, 6253–6259). Another 5'-biotin phosphoramidite, namely [1-N-(4,4'-Dimethoxytrityl)-biotinyl-6-aminohexyl]-2-cyanoethyl-(N,N-diisopropyl)-phosphoramidite, may be used to biotinylate an oligonucleotide. This compound is sold by Glen Research under license from Zeneca PLC.

In another embodiment, for example, the affinity group is a chelate of divalent or trivalent cations ($Ni^{2+}$, $Cu^{2+}$, $Eu^{3+}$, etc.), and a PDLS-coupled globular protein such as ovalbumin, thyroglobulin etc., is used as an affinity binding partner (Dahlen et al.,1994, Bioconjug. Chem. 5:268–72; Li and Selvin, 1997, Bioconjug, Chem. 8:127–32; Lamture and Wensel, 1995, Bioconjug. Chem. 6:88–92).

In another embodiment, the oligonucleotide probe is labeled by incorporation of hapten-labeled nucleotides such as digoxigenin-labeled nucleotides (Holtke and Kessler 1990), and the hapten-labeled bases are detected using an antibody that specifically binds to the hapten, for example anti-DIG-alkaline phosphatase or POD conjugate (Fab fragments). Such compounds can be detected using chemiluminescent, colorimetric, or fluorescent substrates. Some of the affinity labels and reagents for their detection and isolation are available commercially.

In an alternative embodiment, the SNP-specific probe is directly labeled. The detectable labels may be distinct fluorophores ($F_1$ and $F_2$) linked to deoxyribose bases, as depicted in FIG. 2. Direct methods for linking detectable labels to nucleic acids are well known to those of skill in the art. For example, European Patent Publication No. EP 0370 694 A2, entitled, "Diagnostic Kit and Method Using a Solid Phase Capture Means For Detecting Nucleic Acid", by Burdick and Oakes, publication date May 30, 1990, discloses methods of linking such labels to oligonucleotides. For example, fluorophores can be linked to deoxyribonucleotide bases prior to synthesis of the oligonucleotide primer. Direct abeling can be accomplished by incorporating fluorescent dye-labeled phosphoramidites into an oligonucleotide during synthesis. Fluorescently labeled nucleoside analogs are available commercially, or can be produced synthetically, by methods known in the art (see, Brumbaugh et al., 1988, Proc. Natl. Acad. Sci. (USA), 85:5610–5614). Such analogs can be synthesized by derivatizing a 2'-deoxynucleoside through organometallic intermediates to give the 5-dimethoxytrityl adduct. The methyl ester is hydrolyzed, activated, and reacted with an appropriately monoacylated alkyl diamine. Such linker arm nucleosides can be purified, and converted to nucleoside analogs suitable for chemical oligonucleotide synthesis. Two such fluorescein labels are 5'-hexachloro chloro chloro-fluorescein phosphoramidite (HEX), and 5'-tetra chloro-fluorescein phosphoramidite (TET), both available from Glen Research. Oligonucleotides may be synthesized using any method known in the art (see Section 5.4.3). For example, standard phosphoramidite chemistry may be used and reagents may be obtained from any one of many commercial suppliers (e.g., Applied Biosystems 392/394 DNA synthesizer).

5.4.2 SIGNAL AMPLIFICATION AND DETECTION METHODS

For the embodiments presented herein, where two or more markers are present on a single probe, it is important that the two detectable labels are distinguishable. This may be accomplished, for example, by using different fluorophores that emit at different frequencies, as discussed hereinbelow, or by using different types of luminescent agents.

In a preferred embodiment, the detectable label is a luminescent agent. Luminescent agents, depending upon the source of exciting energy, can be classified as radioluminescent, chemiluminescent, bioluminescent, and photoluminescent (including fluorescent and phosphorescent). Various fluorescent dyes known in the art may be used. Two commonly used groups of dyes are the fluorescein-based dyes and the rhodamine-based dyes. Specific, non-limiting examples of fluorophores which can be used are given in Table 1.

TABLE 1

Emission and Absorption Spectra of Commonly Used Fluorophores

| DYE | Absorbance (nm) | Emission (nm) |
| --- | --- | --- |
| fluorescein | 494 | 525 |
| 6-Pam | 494 | 525 |
| Joe | 520 | 548 |
| Tet | 521 | 536 |
| Hex | 535 | 536 |
| Cy3 | 552 | 570 |
| Tamra | 565 | 580 |

TABLE 1-continued

Emission and Absorption Spectra
of Commonly Used Fluorophores

| DYE | Absorbance (nm) | Emission (nm) |
|---|---|---|
| Rox | 568 | 595 |
| Texas red | 587 | 602 |
| Cy5 | 643 | 667 |

In general, fluorescein-based fluorophores tend to absorb short wavelengths (less than 500 nm) and emit photons that have wavelengths approximately 30 nm longer than the absorbed photons, while rhodamine-based fluorophores absorb in the green/yellow range and emit at energies close to that of the absorbed photons (less than 25 nm difference). When using more than one fluorophore, care must be taken in choosing compatible fluorophores to avoid cross-quenching, the result of the emission wavelength of one fluorophore being in the range of the absorption spectra of another fluorophore. In that case, only the emission of the second fluorophore will be detected. Thus, in the most preferred embodiment, the labels are two fluorophores that absorb the same wavelength but emit at different frequencies.

Any method known in the art may be used for visualization or detection of a signal from the detectable label. In one embodiment, the detectable label can be measured by a spectroscopic device. For example, fluorescence can be measured by a device, such as a fluorimeter, or a flow cytometer. Methods for performing assays on fluorescent materials are well known in the art and are described in, e.g., Lackowicz, J. R., 1983, Principles of Fluorescence Spectroscopy, New York:Plenum Press. In another embodiment, the detectable label may be detected by confocal microscopy.

5.4.3 OLIGONUCLEOTIDES AND OLIGONUCLEOTIDE ANALOGS

The oligonucleotide probe used in conjunction with the methods of the invention are often oligonucleotides ranging from 10 to about 100 nucleotides in length. In specific aspects, an oligonucleotide is 10 nucleotides, 15 nucleotides, 20 nucleotides, 50 nucleotides, or 100 nucleotides in length, or up to 50 or 100 nucleotides in length. In the preferred embodiment, the probe is approximately 50 nucleotides in length. An oligonucleotide can be DNA or RNA or chimeric mixtures or derivatives or modified versions thereof, or single-stranded or double-stranded, or partially double-stranded. An oligonucleotide can be modified at the base moiety, sugar moiety, or phosphate backbone, or a combination thereof. An oligonucleotide may include other appending groups, such as biotin, fluorophores, or peptides. Where modified oligonucleotides are used, consideration should be given to the effects in enzyme activity (e.g., S1 nuclease, endo V, etc.) such modifications may have.

An oligonucleotide or derivative thereof used in conjunction with the methods of this invention may be synthesized using any method known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16, 3209), methylphosphonate oligonucleotides can be prepared by use of controlled pore glass polymer supports (Sarin et al., 1988, Proc. Nat'l Acad. Sci. U.S.A. 85, 7448–7451), etc. An oligonucleotide may be an α-anomeric oligonucleotide. An α-anomeric oligonucleotide forms specific double-stranded hybrids with complementary RNA in which, contrary to the usual β-units, the strands run parallel to each other (see Gautier et al., 1987, Nucl. Acids Res. 15, 6625–6641).

Oligonucleotides may be synthesized using any method known in the art (e.g., standard phosphoramidite chemistry on an Applied Biosystems 392/394 DNA synthesizer). Further, reagents for synthesis may be obtained from any one of many commercial suppliers. Spacer phosphoramidite molecules may be used during oligonucleotide synthesis, e.g., to bridge sections of oligonucleotides where base pairing is undesired or to position labels or tags away from an oligonucleotide portion undergoing base pairing. The spacer length can be varied by consecutive additions of spacer phosphoramidites. Spacer phosphoramidite molecules may be used as 5'- or 3'-oligonucleotide modifiers. Such spacers include Spacer Phosphoramidite 9 (i.e., 9-O-Dimethoxytrityl-triethyleneglycol, 1-[(2-cyanoethyl)-(N,N-diisopropyl)]-phosphoramidite, and Spacer Phosphoramidite 18 (i.e., 18-O-Dimethoxytrityl-hexaethyleneglycol, 1-[(2-cyanoethyl)-(N,N-diisopropyl)]-phosphoramidite), both available from Glen Research (Sterling, Va.).

Other spacers are available for use in standard oligonucleotide synthesis. For example, Spacer Phosphoramidite C3 and dSpacer Phosphoramidite can be used to destabilize undesirable self-hybridization events within oligonucleotide probes or to destabilize false hybridization events between incorrectly-matched template/probe complexes. This spacer is available from Glen Research, (i.e., 3-O-Dimethoxytrityl-propyl-1-[(2-cyanoethyl)-(N,N-diisopropyl)]-phosphoramidite), and can be added to substitute for an unknown base within an oligonucleotide sequence.

A branching spacer may be used as one method to increase label incorporation into an oligonucleotide. Such a branching spacer may also be used to increase a detectable signal by hybridization through multiply branched probes. Branching spacers are also available commercially, e.g., from Glen Research.

Biotinylated oligonucleotides are well known in the art. An oligonucleotide may be biotinylated using a biotin-NHS ester procedure. Alternatively, biotin may be attached during oligonucleotide synthesis using a biotin phosphoramidite (Cocuzza, 1989, Tetrahed. Lett. 30, 6287–6290). One such biotin phosphoramidite available from Glen Research is 1-Dimethoxytrityloxy-2-(N-biotinyl-4-aminobutyl)-propyl-3-O-( 2-cyanoethyl)-(N,N-diisopropyl)-phosphoramidite. This compound also has a branch point to allow further additions. The branched spacer used in this biotin phosphoramidite has been described by Nelson et al (1992, Nucl. Acids Res. 20, 6253–6259).

Another 5'-biotin phosphoramidite, namely [1-N-(4,4'-Dimethoxytrityl)-biotinyl-6-aminohexyl]-2-cyanoethyl-(N,N-diisopropyl)-phosphoramidite, may be used to biotinylate an oligonucleotide. This compound is sold by Glen Research under license from Zeneca PLC.

An oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

An oligonucleotide may comprise at least one modified phosphate backbone elected from the group including but not limited to a phosphorothioate, a hosphorodithioate, a phosphoramidothioate, a phosphoramidate, a phosphordiamidate, a ethylphosphonate, an alkyl phosphotriester, and a formacetal or analog thereof.

5.4.4 LINKING OLIGONUCLEOTIDES WITH PEPTIDES

Labeled oligonucleotides have long been used for detection of specific sequences. For example, Burdick and Oakes (Diagnostic kit and method using a solid phase capture means for detecting nucleic acids, European Patent Publication No. EP 0370 694 A2, published May 30, 1990) disclose the use of labeled oligonucleotides, with specific nucleic acid sequences which are complementary to a predetermined sequence of interest. Methods for manipulating nucleic acids on antibody solid phase supports using peptide-labeled oligonucleotides have been described previously (see pending U.S. Pat. application, application Ser. No. 09/174,328, by Iris and Pourny, filed Sept. 16, 1998, which is incorporated herein by reference in its entirety).

In a preferred embodiment, a peptide label is linked to an oligonucleotide probe. The peptide label is used as an affinity label for binding to chip-based antibody arrays. Methods of attaching peptides to oligonucleotides are well known to those with ordinary skill in the art, see, e.g., Soukchareun S. et al., 1995, Bioconjug. Chem. 6:43–53; Tung CH et al., 1991, Bioconjug. Chem. 2:464–465; Bruick RK et al, 1996, Chem. Biol. 3:49–56; Tung CH et al., 1995, Bioconjug. Chem. 6:292–295; Robles J. et al., Bioconjug. Chem., 1997, 8:785–788; and Rajur S. B., et al., 1997, Bioconjug. Chem. 8:935–940.

Oligonucleotides linked to various peptides for use in the methods of this invention may be obtained for example, from Cybergene S.A. (11 rue Claude Bernard, z1 nord, 35400, Saint Mallo, France) and Glen Research (22825 Davis Drive, Sterling, Va. 20164). Further information from Glen Research can be obtained through their web site (http:\\www.glenres.com).

One specific method for linking a peptide to an oligonucleotide recommended by Glen Research is as follows (see also, http:\\www.glenres.com). A heterobifunctional crosslinking reagent is used to link a synthetic peptide having an N-terminal lysine residue to a 5'-thiol-modified oligonucleotide. Such a crosslinking reagent is N-maleimido-6-aminocaproyl-(2'-nitro, 4'-sulfonic acid) phenyl ester (mal-sac-HNSA). The sodium salt of mal-sac-HNSA is available from Bachem Bioscience. Conveniently, reaction of the mal-sac-HNSA crosslinker with an amino group releases a dianion phenolate (i.e. 1-hydroxy-2-nitro-4-benzene sulfonic acid). This dianion phenolate is also a yellow chromophore. The chromophore feature provides (i) a means for quantifying the extent of completion of the coupling reaction (where greater yellow color intensity corresponds to a more complete coupling reaction), and (ii) an aid in monitoring the extent of separation of an activated peptide (i.e. a peptide crosslinked to mal-sac-HNSA and ready for contacting with a 5'-thiol-modified oligonucleotide) from free crosslinking reagent during gel filtration.

The specific steps employed when using a mal-sac-HNSA crosslinker may be as follows. First, a peptide is synthesized having an N-terminal lysine. Alternatively, a peptide having an internal lysine may be used since the lysine epsilon amino group is actually more reactive than the lysine alpha amino group. Second, an oligonucleotide is synthesized having a 5'-thiol group using methods known in the art. Third, the peptide is reacted with an excess of mal-sac-HNSA in a sodium phosphate buffer (pH 7.1). Fourth, the peptide-mal-sac conjugate is separated from free crosslinker and the buffer is exchanged to sodium phosphate (pH 6) using a gel filtration column (e.g. NAP-5, Pharmacia, Uppsala, Sweden). Fifth, a thiol-modified oligonucleotide is activated, desalted and buffer-exchanged to sodium phosphate (pH 6) on a gel filtration column. Sixth, the activated peptide is reacted with the thiol-modified oligonucleotide. Finally, the peptide-oligonucleotide conjugate is purified by ion exchange chromatography (e.g. Nucleogen DEAE-500–10 or equivalent). The elution order from the ion exchange column is as follows: free peptide first, peptide-labeled oligonucleotide next, and free oligonucleotide last.

5.5 ADDRESSABLE ANTIBODY ARRAYS

An addressable array, as used in the invention, comprises a plurality of distinct polypeptides attached to precise locations on a solid phase surface, such as a plastic chip. The position of each distinct polypeptide on the surface is known and therefore "addressable". In the preferred embodiment, the polypeptides are distinct antibodies that have specific affinity for the peptide-linked oligonucleotide probes.

The solid phase surface may be of any material, including, but not limited to, plastic, polycarbonate, polystyrene, polypropylene, polyethlene, glass, nitrocellulose, dextran, nylon, metal, and photolithographic materials. The solid phase surface is preferably a chip, but may also comprise an alternative configuration such as beads, membranes, microparticles, the interior surface of a reaction vessel such as a microtiter plate, test tube or other reaction vessel.

In a preferred embodiment, the antibodies are covalently linked to a plastic chip through their Fc domains. In another embodiment, antibodies are adsorbed onto the chip. Methods of constructing protein arrays, including antibody arrays, are known in the art (see, e.g., Fodor et al., 1996, "Photolabile nucleoside and peptide protecting groups", U.S. Pat. No. 5,489,678; Barret et al., 1993, "Spatially-addressable immobilization of anti-ligands on surfaces", U.S. Pat. No. 5,252,743; Blawas and Reichert, 1998, "Protein patterning", Biomaterials 19:595–609; Blawas et al., 1996, "Patterning antibodies for multiple analyte sensor via photodeprotection chemistry", San Jose: SPIE; Delamarche et al., 1996, "Immobilization of antibodies on a photoactive self-assembled monolayer on gold", Langmuir 12, 1997–2006; Firestone et al., 1996, "Film architecture in biomolecular assemblies, Effect of linker on the orientation of genetically engineered surface-bound proteins", J. Amer. Chem. Soc.18, 9033–9041; Mooney et al., 1996, Patterning of functional antibodies and other proteins by photolithography of silane monolayers, Proc. Natl. Acad. Sci. 93,12287–12291; Pirrung et al, 1996, "A general method for the spatially defined immobilization of biomolecules on glass surfaces using 'caged' biotin", Bioconjugate Chem. 7, 317–321; Gao et al, 1995, "Immunosensing with photoimmobilized immunoreagents on planar optical wave guides", Biosensors Bioelectron 10, 317–328; Schena et al, 1995, "Quantitative monitoring of gene expression patterns with a complementary DNA microarray", Science 270, 467–470; Lom et al., 1993, "A versatile technique for patterning biomolecules onto glass coverslips", J. Neurosci. Methods, 385–397; Pope et al., 1993, "New applications of silane coupling agents for covalently binding antibodies to glass and cellulose solid phase surfaces", Bioconjugate Chem. 4, 116–171; Schramm et al., 1992, "Antibody-antigen complex formation with immobilized immunoglobulins", Anal. Biochem. 205, 47–56; Gombotz et al., 1991, Protein adsorption to poly(ethylene oxide) surfaces, J. Biomed. Mater. Res. 25, 1547–1562; Alarie et al., 1990, "Evaluation of antibody immobilization techniques for fiber optic-based fluoroimmunosensing", Analy. Chim. Acta 229, 169–176; Owaku et al, 1993, Optical immunosensing for IgG, Sensors Actuators B, 13–14, 723–724; Bhatia et al., 1989, "Use of thiol-terminal silanes and heterobifunctional cross linkers for immobilization of antibodies on silica surfaces", Analy. Biochem. 178, 408–413; Lin et al., 1988, "Characterization of immobilized antibodies on silica surfaces", IEEE Trans. Biomed. Engng., 35(6), 466–471).

In a preferred embodiment, the antibodies are arrayed on a "plastic" chip comprised of electronically activated copolymers of a conductive polymers and an antibodies. Such arrays are known in the art and have been used to link polynucleotides to solid supports for polynucleotide based arrays (U.S. Pat. No. 5,837,859 issued Nov. 17, 1998; PCT publication WO 94/22889 dated Oct. 13, 1994). The arrayed pattern may be computer generated and stored. The chips may be prepared in advance and stored in PBS at 4° C. The antibody array chip can be regenerated and used repeatedly. For example, peptides can be released by contacting a pH gradient with the chip causing the antibodies to release the trapped peptides. The chip is then thoroughly rinsed in phosphate buffered saline for storage or immediate reuse.

5.5.1 ANTIBODIES AND PEPTIDES

Antibodies of use with the methods of this invention include any antibodies known in the art. Such antibodies are typically used, for example, to manipulate the nucleic acids of interest. In this regard, a nucleic acid may be manipulated by antibody binding to a portion of the nucleic acid itself or to another antigen (e.g., a protein, peptide or hapten) which is bound (either covalently or non-covalently) to the nucleic acid. In a preferred embodiment, nucleic acids are manipulated using peptide antigens covalently attached to oligonucleotide probes. Such antibodies include but are not limited to polyclonal, monoclonal, chimeric and humanized antibodies, as described below. Further, single chain antibodies, Fab fragments and F(ab')$_2$ fragments, fragments produced by a Fab expression library, anti-idiotypic (anti-Id) antibodies, and epitope-binding fragments of any of the above may also be used.

Polyclonal antibodies which may be used with the invention are heterogeneous populations of antibody molecules derived from the sera of immunized animals. Various procedures well known in the art may be used for the production of polyclonal antibodies to an antigen-of-interest. For example, the production of polyclonal antibodies, various host animals can be immunized by injection with an antigen of interest or derivative thereof, including but not limited to rabbits, mice, rats, etc. Various adjuvants may be used to increase the immunological response, depending on the host species, and including but not limited to Freud's (complete and incomplete), mineral gels such as aluminum hydroxide, surface active substances such as lysolecithin, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies which may be used with the invention are homogeneous populations of antibodies to a particular antigen. A monoclonal antibody (mAb) to an antigen-of-interest can be prepared by using any technique known in the art which provides for the production of antibody molecules by continuous cell lines in culture. These include but are not limited to the hybridoma technique originally described by Kohler and Milstein (1975, Nature 256: 495–497), the more recent human B cell hybridoma technique (Kozbor et al., 1983, Immunology Today 4:72), and the EBV-hybridoma technique (Cole et al., 1985, *Monoclonal Antibodies and Cancer Therapy*, Alan R. Liss, Inc., pp. 77–96). Such antibodies may be of any immunoglobulin class including IgG, IgM, IgE, IgA, IgD and any subclass thereof. The hybridoma producing the mAbs of use in this invention may be cultivated in vitro or in vivo.

Monoclonal antibodies which may be used with the methods of the invention include but are not limited to human monoclonal antibodies. Human monoclonal antibodies may be made by any of numerous techniques known in the art (e.g., Teng et al., 1983, Proc. Natl. Acad. Sci. U.S.A. 80, 7308–7312; Kozbor et al., 1983, Immunology Today 4, 72–79; Olsson et al, 1982, Meth. Enzymol. 92, 3–16).

A chimeric antibody may be used with the methods of the invention. A chimeric antibody is a molecule in which different portions are derived from different animal species, such as those having a variable region derived from a murine mAb and a human immunoglobulin constant region. Various techniques are available for the production of such chimeric antibodies (see, e.g., Morrison et al., 1984, Proc. Natl. Acad. Sci. U.S.A. 81:6851–6855; Neuberger et al., 1984, Nature, 312:604–608; Takeda et al., 1985, Nature 314:452–454) by splicing the genes from a mouse antibody molecule of appropriate antigen specificity together with genes from a human antibody molecule of appropriate biological activity.

A humanized monoclonal antibody may be used with the methods of the invention. Humanized antibodies are antibody molecules from non-human species having one or more complementarily determining regions (CDRs) from the non-human species and a framework region from a human immunoglobulin molecule. Briefly, an immunoglobulin light or heavy chain variable region consists of a "framework" region interrupted by three hypervariable regions, referred to as complementarity determining regions (CDRs). The extent of the framework region and CDRs have been precisely defined (see, Karat et al, 1983, Sequences of proteins of immunological interest, U.S. Department of Health and Human Services). Various techniques have been developed for the production of humanized antibodies (see, e.g., Queen, U.S. Pat. No. 5,585,089; Winter, U.S. Pat. No. 5,225,539, which are incorporated herein by reference in its entirety).

Alternatively, techniques described for the production of single chain antibodies (U.S. Pat. No. 4,946,778; Bird, 1988, Science 242:423–426; Huston et al., 1988, Proc. Natl. Acad. Sci. U.S.A. 85:5879–5883; and Ward et al., 1989, Nature 334:544–546) can be adapted to produce single chain antibodies useful in the device of the invention. Single chain antibodies are formed by linking the heavy and light chain fragments of the Fv region together via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al, 1989, Science 246:1275–1281) to allow rapid and easy identification of monoclonal Fab fragments with the desired specificity.

Further general methods of antibody production and use are suitable for use in connection with the methods of the invention. For example, see Harlow and Lane, 1988, *Antibodies: A Laboratory Manual*, Cold Spring Harbor Laboratory Press, Cold Spring Harbor, N.Y., which is incorporated herein by reference in its entirety.

The single-letter amino acid code corresponds to the three-letter amino acid code of the Sequence Listing set forth hereinbelow, as follows: A, Ala; R, Arg; N, Asn; D, Asp; B, Asx; C, Cys; Q, Gln; E, Glu; Z, Glx; G, Gly; H, His; I, Ile; L, Leu; K, Lys; M, Met; F, Phe; P, Pro; S, Ser; T, Thr; W, Trp; Y, Tyr; and V, Val.

Suitable antibodies for use with the methods of this invention include the following, available from Affinity Bioreagents, Inc., 79, rue des Morillons, 75015, Paris, France.

1) Catalog No. PA 1-047 (affinity-purified rabbit IgG). The corresponding peptide recognized by this Ab is KFSREKKAAKT (SEQ ID NO:1).
2) Catalog No. PA 1-039 (affinity-purified rabbit immunogobins). The corresponding peptide recognized by this Ab is DQKRYHEDIFG (SEQ ID NO:2).
3) Catalog No. PA 1-036 (purified rabbit IgG). The corresponding peptide recognized by the Ab is DLKEEKDINNNVKKT (SEQ ID NO:3).
4) Catalog No. PA 1-014 (purified rabbit antibody). The corresponding peptide recognized by this Ab is CTGEEDTSE (SEQ ID NO: 4).
5) Catalog No. PA 3-013 (affinity purified IgG). The corresponding peptide recognized by this Ab is PEETQTQDQPM (SEQ ID NO:5).
6) Catalog No. PA 1-815 (rabbit anti-serum). The corresponding peptide recognized by this Ab is QKSDQGVEGPGAT (SEQ ID NO:6).
7) Catalog No. PA 3-034 (rabbit polyclonal serum IgG). The corresponding peptide recognized by this Ab is DIGQSIKKFSKV (SEQ ID NO:7). This polyclonal antibody will also recognize QRADSLSSHL (SEQ ID NO:8).

In addition, antibodies for use with the methods of this invention may be obtained from Medical & Biological Laboratories Co., Ltd., 440 Arsenal Street, Watertown, Mass. 02171, U.S.A. These include the following:

1) Code No. 561 (Rabbit IgG from anti-serum). The corresponding peptide recognized is YPYDVPDYA (SEQ ID NO:9).
2) Code No. 562 (Rabbit IgG from anti-serum). The corresponding peptide recognized is EQKLISEEDL (SEQ ID NO:10).
3) Code No. 563 (Rabbit IgG from anti-serum). The corresponding peptide recognized is YTDEMNKLGK (SEQ ID NO: 11).

5.6 TARGET GENETIC DISORDERS

In one embodiment, the high-throughput SNP screening method of the invention is used for diagnosis of genetic disorders in patients' samples. Non-limiting examples of genetic disorders that can be tested using this method include hereditary diseases such as cystic fibrosis, Tay-Sachs disease, sickle cell anemia, hemophelia, atherosclerosis, diabetes, and obesity. Such hereditary diseases may include degenerative and non-degenerative neurological diseases such as Alzheimer's disease, Parkinson's disease, amyotrophic lateral sclerosis, Huntington's disease, Wilson's disease, spinal cerebellar ataxia, Friedreich's ataxia and other ataxias, prion diseases including Creutzfeldt-Jakob disease, dentatorubral pallidoluysian atrophy, spongiform encephalopathies, myotonic dystrophy, depression, schizophrenia, and epilepsy. Hereditary diseases may also include metabolic diseases such as, for example, hypoglycemia or phenylketonuria. Cardiovascular diseases and conditions are also included, non-limiting examples of which include atherosclerosis, myocardial infarction, and high blood pressure. The invention can further be used for detection and diagnosis of Lyme disease, tuberculosis, and sexually transmitted diseases.

In another embodiment, the SNP detection methods of the invention can be used for determining the genetic basis of a disease or disorder. For example, the SNP detection methods can be used to detect and compare polymorphisms present in patients afflicted with a disorder whose genetic basis is not known. This application of the multiplex PCR-free SNP detection method is particularly useful for complex disorders, where more than one genetic loci may contribute to the phenotype. Once the contributory genetic loci are determined, the SNP detection methods can further be useful in early detection and treatment of such diseases. Non-limiting examples of target disorders of clinical interest include asthma, arthritis, psoriasis, excema, allergies, drug resistance, drug toxicity, and cancers such as, but not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g. acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

The SNP detection methods can further be useful in determining genetic differences and diagnosis of patients with autoimmune diseases, including but not limited to, insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease.

Genotyping screening methods may also be used screening for specific SNPs not associated with disease. Non-limiting examples include SNPs present in non-coding genomic sequences, or SNPs associated with different human blood groups.

In a preferred aspect of the invention, the methods of the invention may have particular utility in the identification of human SNPs. It is appreciated, however, that the methods described herein will be useful in diagnosing diseases of other mammals, for example, farm animals including cattle, horses, sheep, goat, and pigs, household pets including cats and dogs, and plants including agriculturally important plants and garden plants.

6. EXAMPLE

Analysis of Pcr-free Genotype Mapping

To demonstrate how the methods of the invention are analyzed for the presence of polymorphisms in a DNA sample, the following example is provided. The steps described herein are shown schematically in FIG. 2. Methods for preparation and labeling of probes and for carrying out the enzymatic reactions are described in detail in Section 5 herein above. The single nucleotide polymorphism (SNP) of interest in this example is a G/C base-pair polymorphism located at a site where the normal, wild-type (WT) base pair is A/T.

As shown in FIG. 2, a peptide-labeled oligonucleotide "positive probe" is synthesized having a G at the SNP site. The probe has two fluorophores, $F_1$ and $F_2$, positioned on the second nucleotide from the 5' end and on the 3' end, respectively, as shown in FIG. 2. A second peptide-labeled oligonucleotide is prepared having the same sequence but with a T at the SNP site. This probe is the "negative probe". The negative probe is labeled with the same fluorophores as the positive probe, at precisely the same positions.

In the first nucleic acid sample to be analyzed, the SNP occurs on both copies of the gene. The probes are annealed to aliquots of the target DNA sample in separate reactions. After binding to antibody chips, or a single antibody chip with addressable loci, and samples are digested with mung bean nuclease to remove the overhanging ends. A first reading is taken to detect signals from the two fluorophores. The readout is expressed as a ratio of signal from sample, normalized to a known SNP control sample. Since both the positive and the negative probes retain both fluorophores, the first reading ($R_1$) for both samples is expected to be 1.0 (see Table 2 below).

TABLE 2

|  | $R_1$ | $R_2$ |
|---|---|---|
| Positive SNP Probe (G) | | |
| F1 | 1.0 | 1.0 |
| F2 | 1.0 | 1.0 |
| Negative WT Probe (T) | | |
| F1 | 1.0 | 1.0 |
| F2 | 1.0 | 0 |

The chip is then immersed in a solution containing S1 nuclease (S1) and Endonuclease V (Endo V), which results in strand scission at mismatched base pairs. The enzymes will not cleave the SNP site of the positive SNP probe, since the target DNA will have the same sequence as the probe. However, the negative probe will be cleaved at the SNP site since the wild type base T of the probe will not pair with the G of the target DNA. Thus, the positive probe retains both fluorophores, whereas the negative probe retains only the F1 fluorophore. A second reading is taken ($R_2$). Again, as with the first reading, a control sample that has not been treated with nuclease provides a baseline reading. The readout is expressed as the signal relative to a baseline reading from the control sample where the antibody chip was not treated with enzymes, and the expected results are shown in Table 2 below.

To determine whether a SNP is present, a ratio of F2 to F1 is calculated for each probe and each reading, as shown in the top columns of the two charts in Table 3. For the SNP probe the expected F2/F1 ratio is 1.0 for R1 and 1.0 for R2. The two ratios are compared. If the first ratio is at least 20% greater than the second ratio then a mismatch is identified. More preferably, the first ratio is at least 25%, or most preferably 35% greater, than the second ratio to identify a mismatch. Here, no mismatch is identified. Thus, the DNA is the same as the probe, i.e., it contains the polymorphic SNP site. To confirm this result, the same calculation is made with the negative WT probe. For the WT probe the expected F2/F1 ratio is 1 for R1 and 0 for R2. The two ratios are compared. If the $R_1$ ratio is at least 20% greater than the R2 ratio then a mismatch is identified. More preferably, the $R_1$ ratio is at least 25% greater, or most preferably 35% greater, than the the R2 ratio to identify a mismatch. Since 1 is greater than 0, a mismatch is identified, the target DNA is not wild type, confirming the result with the positive probe.

Using a target DNA sample with a wild type base at the SNP site, the opposite result is expected to be obtained with both probes. Typical expected results are shown in the lower panels of the charts in Table 3.

TABLE 3

| Target DNA | $R_1$ | $R_2$ |
|---|---|---|
| Positive SNP Probe (G) | | |
| T/A (SNP) | 1.0 | 1.0 |
| G/C (wild type) | 1.0 | 0 |
| Negative WT Probe (G) | | |
| T/A (SNP) | 1.0 | 0 |
| G/C (wild type) | 1.0 | 1.0 |

The analysis is the same even in experiments using more complex target DNA samples. For example, a DNA sample with a heterozygote genotype, i.e., where the target DNA sample contains one allele with a SNP and the other allele with a WT base, can be mapped using this method. In this case, half the hybrids will have mismatched base pairs at the SNP site in experiments using either the positive SNP probe or the negative WT probe, and thus only half the probes in any sample will be cleaved with S1 and Endo V. Again, the ratio of F2 to F1 is calculated for each probe and each reading, as shown in the middle columns of the two charts in Table 4, below. For the SNP probe the expected F2/F1 ratio is 1.0 for R1 and 0.5 for R2. The two ratios are compared. If the first ratio is at least 20% greater than the second ratio then a mismatch is identified. More preferably, the first ratio is at least 25%, or most preferably 35% greater, than the second ratio to identify a mismatch. Here, a mismatch is identified. The same calculation is made with the negative WT probe. For the WT probe the expected F2/F1 ratio is again 1.0 for R1 and 0.5 for R2. Again, where the R1 ratio is at least 20%, or preferably, 25%, or more preferably, 35% greater than the R2 ratio and a mismatch is identified. The target DNA is therefore neither entirely wild type nor SNP in genotype. Because the F2/F1 ratio for both probes is again 1.0 for R1 and 0.5 for R2, a heterozygosity is identified. The result can be confirmed using control target DNA samples with homozygous WT and SNP alleles. The expected results for all three possible genotypes are shown in Table 4 below.

TABLE 4

| Allele$_1$ | Allele$_2$ | R$_1$ | R$_2$ |
|---|---|---|---|
| Positive SNP Probe (G) | | | |
| G/C (wild type) | G/C (wild type) | 1.0 | 1.0 |
| G/C (wild type) | T/A (SNP) | 1.0 | 0.5 |
| T/A (SNP) | T/A (SNP) | 1.0 | 0 |
| Negative WT Probe (A) | | | |
| G/C (wild type) | G/C (wild type) | 1.0 | 0 |
| G/C (wild type) | T/A (SNP) | 1.0 | 0.5 |
| T/A (SNP) | T/A (SNP) | 1.0 | 1.0 |

Similar analysis is used to compare more complex populations of target DNA samples. For example, in one embodiment of the invention, the multiplex PCR-free SNP detection method is used to associate a particular disorder with a genotype. In this case, two target DNA samples are compared—a sample comprising a plurality of DNA samples from a population afflicted with the disorder of interest, and a control sample obtained from a non-afflicted population. The analysis, as described above, is used to detect differences in a plurality of SNP sites between the two populations. The presence of a SNP site in the afflicted population, but absent in the control population allows correlation of said SNP site with the disorder.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated by reference into the present application in its entirety.

SEQUENCE LISTING

```
<160> NUMBER OF SEQ ID NOS: 11

<210> SEQ ID NO 1
<211> LENGTH: 11
<212> TYPE: PRT
<213> ORGANISM: RABBIT

<400> SEQUENCE: 1

Lys Phe Ser Arg Glu Lys Lys Ala Ala Lys T hr
 1               5                  10

<210> SEQ ID NO 2
<211> LENGTH: 11
<212> TYPE: PRT
<213> ORGANISM: RABBIT

<400> SEQUENCE: 2

Asp Gln Lys Arg Tyr His Glu Asp Ile Phe G ly
 1               5                  10

<210> SEQ ID NO 3
<211> LENGTH: 15
<212> TYPE: PRT
<213> ORGANISM: RABBIT

<400> SEQUENCE: 3

Asp Leu Lys Glu Glu Lys Asp Ile Asn Asn A sn Val Lys Lys Thr
 1               5                  10                  15

<210> SEQ ID NO 4
<211> LENGTH: 9
<212> TYPE: PRT
<213> ORGANISM: RABBIT

<400> SEQUENCE: 4
```

-continued

Cys Thr Gly Glu Glu Asp Thr Ser Glu
 1               5

<210> SEQ ID NO 5
<211> LENGTH: 11
<212> TYPE: PRT
<213> ORGANISM: RABBIT

<400> SEQUENCE: 5

Pro Glu Glu Thr Gln Thr Gln Asp Gln Pro Met
 1               5                   10

<210> SEQ ID NO 6
<211> LENGTH: 13
<212> TYPE: PRT
<213> ORGANISM: RABBIT

<400> SEQUENCE: 6

Gln Lys Ser Asp Gln Gly Val Glu Gly Pro Gly Ala Thr
 1               5                   10

<210> SEQ ID NO 7
<211> LENGTH: 12
<212> TYPE: PRT
<213> ORGANISM: RABBIT

<400> SEQUENCE: 7

Asp Ile Gly Gln Ser Ile Lys Lys Phe Ser Lys Val
 1               5                   10

<210> SEQ ID NO 8
<211> LENGTH: 10
<212> TYPE: PRT
<213> ORGANISM: RABBIT

<400> SEQUENCE: 8

Gln Arg Ala Asp Ser Leu Ser Ser His Leu
 1               5                   10

<210> SEQ ID NO 9
<211> LENGTH: 9
<212> TYPE: PRT
<213> ORGANISM: RABBIT

<400> SEQUENCE: 9

Tyr Pro Tyr Asp Val Pro Asp Tyr Ala
 1               5

<210> SEQ ID NO 10
<211> LENGTH: 10
<212> TYPE: PRT
<213> ORGANISM: RABBIT

<400> SEQUENCE: 10

Glu Gln Lys Leu Ile Ser Glu Glu Asp Leu
 1               5                   10

<210> SEQ ID NO 11
<211> LENGTH: 11
<212> TYPE: PRT
<213> ORGANISM: RABBIT

-continued

```
<400> SEQUENCE: 11

Tyr Thr Asp Ile Glu Met Asn Lys Leu Gly L ys
 1               5                  10
```

What is claimed is:

1. A method for high-throughput nucleotide polymorphism identification in a nucleic acid sample from a subject comprising:
   (a) contacting a plurality of peptide-labeled polymorphism-specific oligonucleotide probes with the nucleic acid sample in solution, each probe containing a signal-generating marker, under conditions conducive to hybridization of the probes to nucleic acid in the sample, wherein different probes are labeled with distinguishable peptide labels;
   (b) contacting the probes with an addressable antibody array, said antibody array comprising a solid phase to which are attached antibodies immunospecific to said peptide labels;
   (c) removing probes that are not hybridized to nucleic acid from the sample; and
   (d) after steps (a), (b), and (c), detecting one or more probes that hybridize to nucleic acid in the sample by a method comprising, in the following order:
      i) detecting or measuring from the solid phase one or more signals generated where an antibody has bound to one of said peptide labels;
      ii) removing a marker on probes that are bound to the antibody array and that are hybridized with any mismatches to nucleic acid from the sample by contacting the hybrids with one or more enzymes which cleave at mismatched base parts; and
      iii) detecting or measuring from the solid phase one or more signals generated where an antibody has bound to one of said peptide labels,
      wherein, for each locus where an antibody has bound to one of said peptide labels, if the signal detected or measured in step (d)(i) differs from the signal detected or measured in step (d)(iii), then a nucleotide polymorphism is identified.

2. The method of claim 1, wherein detecting the one or more probes is carried out without using PCR or MutS.

3. A method for screening a nucleic acid sample from one or more subjects for the presence of a polymorphism comprising the following steps in the order stated:
   (a) contacting the nucleic acid sample in solution with one or more nucleotide polymorphism-specific peptide-labeled oligonucleotide probes, under conditions conducive to hybridization of the probes to nucleic acid in the sample, each probe comprising a first marker covalently attached to a first detectable label, and a second marker covalently attached to a second detectable label that produces a signal distinguishable from the first detectable label, such that one or more hybrid molecules are formed between the nucleic acid and one or more oligonucleotide probes;
   (b) capturing at least one of the one or more hybrid molecules on a solid phase surface via the peptide label(s) on the probes(s);
   (c) contacting the solid phase surface with mung bean nuclease, under conditions wherein the nuclease is active;
   (d) removing material not bound to the solid phase surface;
   (e) detecting or measuring from the solid phase surface a first signal from the first detectable label and a second signal from the second detectable label;
   (f) contacting the hybrid molecules on the solid phase surface with one or more enzymes which cleave at mismatched base pairs;
   (g) removing material not bound to the solid phase surface; and
   (h) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio,
   wherein a difference between the first ratio and the second ratio indicates that a polymorphism is identified.

4. A method for screening a nucleic acid sample from one or more subjects for the presence of a polymorphism comprising the following steps in the order stated:
   (a) contacting the nucleic acid sample in solution with one or more nucleotide polymorphism-specific peptide-labeled oligonucleotide probes under conditions conducive to hybridization of the probes to nucleic acid in the sample, each probe comprising a first and a second marker, such that one or more hybrid molecules are formed between the nucleic acid and one or more nucleotide polymorphism-specific oligonucleotide probes;
   (b) capturing at least one of the one or more hybrid molecules on a solid phase surface via the peptide label(s) on the probe(s);
   (c) contacting the solid phase surface with mung bean nuclease, under conditions wherein the nuclease is active;
   (d) removing material not bound to the solid phase surface;
   (e) contacting the hybrid molecules on the solid phase surface with (i) a first partner molecule which specifically binds first marker, and (ii) a second partner molecule which specifically binds the second marker, said first partner molecule comprising a first detectable label and said second partner molecule comprising a second detectable label that produces a signal distinguishable from the first detectable label;
   (f) removing material not bound to the solid phase surface;
   (g) detecting or measuring from the solid phase surface a first signal from the first detectable label and a second signal from the second detectable label;
   (h) contacting the hybrid molecules on the solid phase surface with one or more enzymes which cleave at mismatched base pairs;
   (i) removing material not bound to the solid phase surface; and j) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein a difference between the first ratio and the second ratio indicates that a polymorphism is identified.

5. A method for screening a nucleic acid sample from one or more subjects for the presence of a polymorphism comprising the following steps in the order stated:

(a) contacting the nucleic acid sample in solution with one or more nucleotide polymorphism-specific peptide-labeled oligonucleotide probes, under conditions conducive to hybridization of the probes to nucleic acid in the sample, each probe comprising a first and a second marker, such that one or more hybrid molecules are formed between the nucleic acid and one or more nucleotide polymorphism-specific oligonucleotide probes;

(b) capturing at least one of the one or more hybrid molecules on a solid phase surface via the peptide label(s) on the probe(s);

(c) contacting the solid phase surface with mung bean nuclease, under conditions wherein the nuclease is active;

(d) removing material not bound to the solid phase surface;

(e) contacting the solid phase surface with a first primary partner molecule, which binds the first marker, and a second primary partner molecule which binds the second marker;

(f) removing material not bound to the solid phase surface;

(g) contacting the hybrid molecules on the solid phase surface with (i) a first secondary partner molecule, which binds the first primary partner molecule, said first secondary partner molecule comprising a first detectable label, and (ii) a second secondary partner molecule, which binds the second primary partner molecule, said second secondary partner molecule comprising a second detectable label that produces a signal distinguishable from the first detectable label;

(h) removing material not bound to the solid phase surface;

(i) detecting or measuring from the solid phase surface a first signal from the first detectable label and a second signal from the second detectable label;

j) contacting the hybrid molecules on the solid phase surface with one or more enzymes which cleave at mismatched base pairs;

(k) removing material not bound to the solid phase surface; and (l) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein a difference between the first ratio and the second ratio indicates that a polymorphism is identified.

6. The method of claim 3, 4, or 5, wherein at least one of the one or more nucleotide polymorphism-specific peptide-labeled oligonucleotide probes comprises:

(a) a peptide covalently attached to the 5' end of the oligonucleotide;

(b) a first marker at the penultimate 5' position of the oligonucleotide; and (c) a second marker at the 3'-end of the oligonucleotide.

7. The method of claim 3, 4, or 5, wherein the solid phase surface comprises a plurality of loci, wherein each locus specifically binds to one of the one or more oligonucleotide probes via the peptide of the peptide-labeled oligonucleotide and wherein the peptide is covalently attached to the 5' end of the oligonucleotide.

8. The method of claim 4 wherein the first or second marker is covalently attached to a biotin moiety and the first or second partner molecule is avidin or streptavidin.

9. The method of claim 5 wherein the first or second marker is covalently attached to a biotin moiety and the first or second primary partner molecule is avidin or streptavidin.

10. The method of claim 4 wherein the first or second marker is covalently attached to a carbohydrate moiety and the first or second partner molecule is a lectin.

11. The method of claim 5 wherein the first or second marker is covalently linked to a carbohydrate moiety and the first or second primary partner molecule is a lectin.

12. The method of claim 4 wherein the first partner molecule is an antibody that binds specifically to the first marker and the second partner molecule is an antibody that binds specifically to the second marker.

13. The method of claim 5 wherein the first and second primary partner molecules are distinct primary antibodies, and the first and second secondary partner molecules are distinct secondary antibodies.

14. The method of claim 3, 4, or 5 wherein either or both the first detectable label or the second detectable label is an enzyme, a fluorophore, a chemiluminescent label, or a radioisotope.

15. The method of claim 14, wherein either or both the first detectable label or the second detectable label is a fluorophore.

16. A method for identifying a polymorphism in a nucleic acid sample from one or more subjects comprising the following steps in the order stated:

(a) contacting the nucleic acid sample in solution with one or more nucleotide polymorphism-specific peptide-labeled oligonucleotide probes, under conditions conducive to hybridization of the probes to nucleic acid in the sample; each probe comprising a first marker covalently attached to a first detectable label, and a second marker covalently attached to a second detectable label that produces a signal distinguishable from the first detectable label; such that one or more hybrid molecules are formed between the nucleic acid and one or more oligonucleotide probes;

(b) capturing at least one of the one or more hybrid molecules on a solid phase surface via the peptide label(s) on the probe(s);

(c) contacting the solid phase surface with mung bean nuclease, under conditions wherein the nuclease is active;

(d) removing material not bound to the solid phase surface;

(e) detecting or measuring from the solid phase surface a first signal from the first detectable label and a second signal from the second detectable label;

(f) cleaving the hybrid molecules on the solid phase surface at mismatched base pairs;

(g) removing material not bound to the solid phase surface; and (h) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein the first ratio at least 35% greater than the second ratio indicates that a polymorphism is identified.

17. A method for identifying a polymorphism in a nucleic acid sample from one or more subjects comprising the following steps in the order stated:

(a) contacting the nucleic acid sample in solution with one or more nucleotide polymorphism-specific peptide-labeled oligonucleotide probes under conditions conducive to hybridization of the probes to nucleic acid in the sample; each probe comprising a first and a second marker; such that one or more hybrid molecules are formed between the nucleic acid and one or more nucleotide polymorphism-specific oligonucleotide probes;

(b) capturing at least one of the one or more hybrid molecules on a solid phase surface via the peptide label(s) on the probe(s);

(c) contacting the solid phase surface with mung bean nuclease, under conditions wherein the nuclease is active;

(d) removing material not bound to the solid phase surface;

(e) contacting the solid phase surface with (i) a first partner molecule which specifically binds the first marker, and (ii) a second partner molecule which specifically binds the second marker, said first partner molecule comprising a first detectable label and said second partner molecule comprising a second detectable label that produces a signal distinguishable from the first detectable label;

(f) removing material not bound to the solid phase surface;

(g) detecting or measuring from the solid phase surface a first signal from the first detectable label and a second signal from the second detectable label;

(h) cleaving the hybrid molecules on the solid phase surface at mismatched base pairs;

(i) removing material not bound to the solid phase surface; and (j) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein the first ratio at least 35% greater than the second ratio indicates that a polymorphism is identified.

18. A method for identifying a polymorphism in a nucleic acid sample from one or more subjects comprising the following steps in the order stated:

(a) contacting the nucleic acid sample in solution with one or more nucleotide polymorphism-specific peptide-labeled oligonucleotide probes, under conditions conducive to hybridization of the probes to nucleic acid in the sample; each probe comprising a first and a second marker; such that one or more hybrid molecules are formed between the nucleic acid and one or more nucleotide polymorphism-specific oligonucleotide probes;

(b) capturing at least one of the one or more hybrid molecules on a solid phase surface via the peptide label(s) on the probe(s);

(c) contacting the solid phase surface with mung bean nuclease, under conditions wherein the nuclease is active;

(d) removing material not bound to the solid phase surface;

(e) contacting the solid phase surface with a first primary partner molecule, which binds the first marker, and a second primary partner molecule which binds the second marker;

(f) removing material not bound to the solid phase surface;

(g) contacting the solid phase surface with (i) a first secondary partner molecule, which binds the first primary partner molecule, said first secondary partner molecule comprising a first detectable label, and (ii) a second secondary partner molecule, which binds the second primary partner molecule, said second secondary partner molecule comprising a second detectable label that produces a signal distinguishable from the first detectable label;

(h) removing material not bound to the solid phase surface;

(i) detecting or measuring from the solid phase surface a first signal from the first detectable label and a second signal from the second detectable label;

(j) cleaving the hybrid molecules on the solid phase surface at mismatched base pairs;

(k) removing material not bound to the solid phase surface; and (h) detecting or measuring from the solid phase surface a third signal from the first detectable label and a fourth signal from the second detectable label, determining a first ratio of the second signal to the first signal, and a second ratio of the fourth signal to the third signal, and comparing the first ratio to the second ratio, wherein the first ratio at least 35% greater than the second ratio indicates that a polymorphism is identified.

19. The method of claim 3, 4, 5, 16, 17, or 18, wherein the solid phase surface comprises a plurality of loci, wherein each locus comprises an antibody specific to one or more of the peptides of the peptide-labeled oligonucleotide probes.

20. The method of claim 3, 4, 5, 16, 17, or 18, wherein the solid phase surface is a plastic chip.

21. The method of claim 3, 4, 5, 16, 17, or 18, wherein the solid phase surface is the well of a microtiter plate.

22. The method of claim 1, 3, 4, 5, 16, 17, or 18, wherein the nucleic acid in the sample is less than 2 $\mu$g.

23. The method of claim 1, 3, 4, 5, 16, 17, or 18, wherein the nucleic acid in the sample is selected from the group consisting of genomic DNA and cDNA.

24. The method of claim 23, wherein the nucleic acid in the sample is genomic DNA.

25. The method of claim 23, wherein the nucleic acid in the sample is cDNA.

26. The method of claim 1, 3, 4, 5, 16, 17, or 18, wherein the nucleic acid in the sample is double stranded DNA.

27. The method of claim 1, 3, 4, 5, 16, 17, or 18, wherein the nucleic acid in the sample is single stranded DNA.

28. The method of claim 3, 4, 5, 16, 17, or 18, wherein cleaving the hybrid molecules at mismatched base pairs is carried out by contacting said hybrid molecules with one or more specific nucleases under conditions that allow cleavage of said hybrid molecules at mismatched base pairs.

29. The method of claim 3, 4, 5, 16, 17, or 18, wherein cleaving the hybrid molecules at mismatched base pairs is carried out by contacting said hybrid molecules with *E. coli* endonuclease V and S1 nuclease under conditions that allow cleavage of said hybrid molecules at mismatched base pairs.

30. The method of claim 3, 4, 5, 16, 17, or 18, wherein the first and second detectable labels are fluorophores that absorb at the same wavelength but emit at a distinct frequency.

31. The method of claim 1, 3, or 4 wherein the subject is a plant.

32. The method of claim 1, 3, or 4 wherein the subject is a virus, a bacterium, a yeast, or a fungus.

33. The method of claim 1, 3, or 4 wherein the subject is a mammal.

34. The method of claim 1, 3, or 4 wherein the subject is equine, porcine, ovine, bovine, canine, feline, or human.

35. The method of claim 1, 3, or 4 wherein the subject is a human.

36. The method of claim 1, 3, or 4 wherein the subject is a plurality of human subjects that exhibit a phenotype of interest.

37. The method of claim 3, 4, 5, 16, 17, or 18, wherein the solid phase surface is a silica surface.

* * * * *